United States Patent [19]
Craig et al.

[11] Patent Number: 5,332,664
[45] Date of Patent: Jul. 26, 1994

[54] HUMAN CALCITONIN PRECURSOR POLYPROTEIN STRUCTURAL GENE

[75] Inventors: Roger K. Craig; Iain MacIntyre, both of London, England

[73] Assignee: Celltech Limited, Berkshire, England

[21] Appl. No.: 987,724

[22] Filed: Dec. 8, 1992

Related U.S. Application Data

[63] Continuation of Ser. No. 588,483, Sep. 24, 1990, abandoned, which is a continuation of Ser. No. 233,892, Aug. 12, 1988, abandoned, which is a continuation of Ser. No. 885,312, Jul. 14, 1986, abandoned, which is a continuation of Ser. No. 482,999, Mar. 11, 1983, abandoned.

[30] Foreign Application Priority Data

Jul. 15, 1981 [GB] United Kingdom ............... 8121699
Nov. 26, 1981 [GB] United Kingdom ............... 8135738

[51] Int. Cl.$^5$ .................. C12P 21/02; C07K 7/38; A61K 37/00
[52] U.S. Cl. .................. 435/69.4; 435/69.7; 435/69.1; 435/172.3; 514/12; 530/307
[58] Field of Search .............. 435/69.4, 69.1, 69.7, 435/172.3; 514/12; 530/307

[56] References Cited

U.S. PATENT DOCUMENTS

| Re. 32,347 | 2/1987 | Neher et al. | 514/12 |
|---|---|---|---|
| 4,119,493 | 10/1987 | Isowa et al. | 95/29 |
| 4,320,196 | 3/1982 | Morihara et al. | 435/70 |
| 4,338,397 | 7/1982 | Gilbert et al. | 435/68 |
| 4,709,014 | 11/1987 | Tamaoki | 530/333 |

FOREIGN PATENT DOCUMENTS 0013828 8/1980 European Pat. Off.
WO8304028 11/1983 PCT Int'l Appl.

OTHER PUBLICATIONS

Breddam, Klaus et al., "Amidation of Growth Hormone Releasing Factor (1-29) by Serine Carboxypeptidase Catalysed Transpeptidation", *Int. J. Peptide Protein Res.*, 37, 1991, 153-160.

Klaus Breddam et al., *Carlsberg Res. Commun.*, "Carboxypeptidase Y Catalyzed Transpeptidations and Enzymatic Peptide Synthesis", vol. 45, pp. 237-247 (1980).

Klaus Breddam et al., *Carlsberg Res. Commun.*, "Influence of the Substrate Structure on Carboxypeptide Y Catalyzed Peptide Bond Formation", vol. 45, pp. 361-367 (1980).

Gunther Kreil et al., *Federation Proceedings*, "Biosynthesis of a Secretory Peptide in Honeybee Venom Glands: Intermediates Detected in vivo and in vitro", vol. 36, No. 8, Jul. 1988, 2081-2086.

A. F. Bradbury et al., "Mechanism of C-terminal Amide Formation by Pituitary Enzymes", *Nature*, vol. 298, pp. 686-688 (1982).

Desplan et al., "Cell Free Translation of mRNA Coding for Human and Murine Calcitonin", *FEBS Letters*, 117, No. 1, pp. 89-92 (1980).

Goodman et al., "Cell-Free Translation of Messenger RNA Coding for a Precursor of Human Calcitonin", *Biochem Biophys Res. Commun*, vol. 91, No. 3, pp. 932-938 (1979).

Arama et al., "Characterization of Rat Calcitonin mRNA", *Proc. Natl. Acad. Sci.*, (USA), 77, 4444-4448 (1980).

*Primary Examiner*—Charles L. Patterson, Jr.
*Attorney, Agent, or Firm*—Spencer, Frank & Schneider

[57] ABSTRACT

Production of human calcitonin precursor structural gene, the insertion of this gene in a vector system, the cloning thereof and a process for the production of authentic human calcitonin using recombinant DNA biotechnology.

11 Claims, 16 Drawing Sheets

FIG. IA
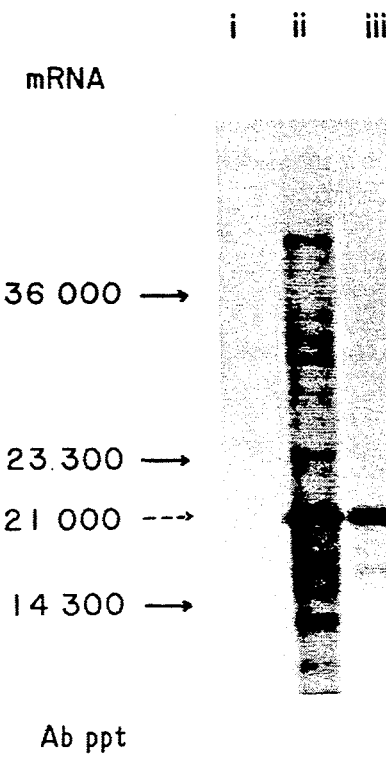
FIG. IB
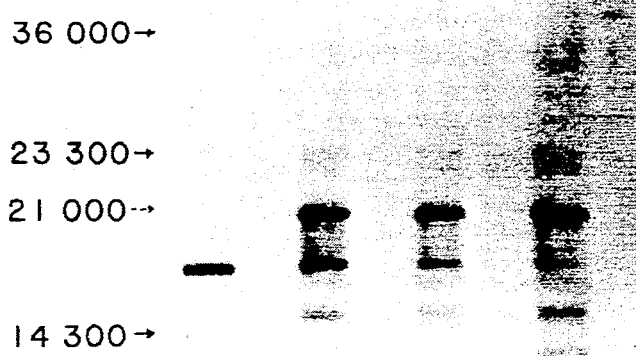
FIG. IC
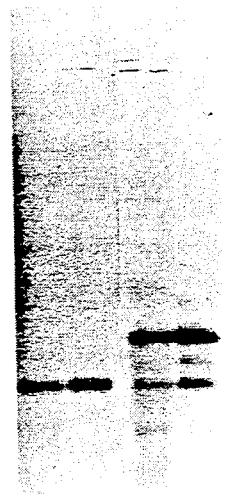

i  ii  iii  iv  v

ORIGIN→

(LINEAR pBR 322 DNA) 4362→
(Pst I/Bam HI pBR 322) 3237→
(18S-rRNA) 2060→
(Pst I/Bam HI pBR 322) 1125→

(E.coli tRNA) 80→

```
         -36 -35 -34 -33 -32 -31 -30 -29 -28 -27 -26 -25 -24 -23 -22 -21 -20 -19 -18 -17 -16 -15 -14 -13 -12 -11 -10 -9
         Val Leu Leu Ala Ala Leu Val Gln Asp Tyr Val Gln Met Lys Ala Ser Glu Leu Glu Gln Gln Glu Arg Glu Gly Ser Ser
      5'GTC CTG CTG GCT GCA CTG GTG CAG GAC TAT GTG CAG ATG AAG GCC AGT GAG CTG GAG CAG CAA GAG AGA GAG GGC TCC AGC
      3'CAG GAC GAC CGA CGT GAC CAC GTC CTG ATA CAC GTC TAC TTC CGG TCA CTC GAC CTC GTT CTC TCT CTC CCG AGG TCG

-8  -7  -6  -5  -4  -3  [-2  -1]  1   2   3   4   5   6   7   8   9   10  11  12  13  14  15  16  17  18  19  20  21  22  23
      Leu Asp Ser Pro Arg Ser [Lys Arg] Cys Gly Asn Leu Ser Thr Cys Met Leu Gly Thr Tyr Thr Gln Asp Phe Asn Lys Phe His Thr Phe Pro
      CTG GAC AGC CCC AGA TCT AAG CGG TGC GGT AAT CTG AGT ACT TGC ATG CTG GGC ACA TAC ACG CAG GAC TTC AAC AAG TTC CAC ACG TTC CCC
      GAC CTG TCG GGG TCT AGA TTC GCC ACG CCA TTA GAC TCA TGA ACG TAC GAC CCG TGT ATG TGC GTC CTG AAG TTG TTC AAG GTG TGC AAG GGG 24  25  26  27  28  29  30  31  32   +1  +2  +3  +4   +5  +6  +7  +8  +9  +10 +11 +12 +13 +14 +15 +16 +17 +18 +19 +20 +21 +22
      Gln Thr Ile Ala Gly Val Ala Pro [Gly Lys Lys Arg] Asp Met Ser Ser Asp Leu Glu Arg Asp His Arg Pro His Val Ser Met Pro Gln
      CAA ACT ATT GCA GGA GTT GGG GCA CCT GGA AAG AAA AGG GAT ATG TCC AGC GAT TTG GAG AGA GAC CAT CGC CAT GTT AGC ATG CCC CAG
      GTT TGA CGT TAA CCC CAA GGT CCT GGA CCT TTC TTT TCC CTA TAC AGG TCG CTA AAC CTC TCT CTG GTA GCG GTA CAA TCG TAC GGG GTC

+23 +24 +25
      Asn Ala Asn term
      AAT GCC AAC TAA ACTCCTCCCCTTTCCTTCCTTCTTGCATCCTTCCTATAACTTGATGCATGTGGTTTGGTTCCTCTGGCTGCTCTTTGGGCTGGACCACCGAAAG
      TTA CGG TTG ATT TGAGGAGGGGAAAGGAAGAAGTTGAACTACGTACACCAAGGAGACCGACGAGAAACCGACCATAACCACCGAAAG CTTGTGGCAGAGGATGTCTCAAGACTTGAAGTTCTACCCTCGAGTGTCCAACCTTCTTAGTGGAAGAGAATACCAGAAAATGAGGGCCGCTTTGAGTCCCCAGAGATGT
      GAACACCGTCTCCTACAGAGTTCTGAACTTCAAGATGGGAGCTCACAGGTTGGAAGAATCACCTTCTCTTATGGTCTTTTACTCCCGGCGAAACTCAGGGGTCTCTACA CATCAGAGCTCCTCGTCCTGCTTCTGAATGTGCTGATCATTTGAGGAATAAAATTATTTTCCCC(A)n 3'
      GTAGTCTCGAGGAGACAGGACGAAGACTTACACGACTAGTAAACTCCTTATTT TAATAAAAAGGGG(T)n 5'
```

FIG. 4A

HUMAN CALCITONIN PRECURSOR POLYPROTEIN STRUCTURAL GENE

This is a continuation of application Ser. No. 07/588,483 filed Sep. 24, 1990, which is a continuation of application Ser. No. 07/233,892, filed Aug. 12, 1988, which is a continuation of application Ser. No. 06/885,312, filed Jul. 14, 1986, which is a continuation of application Ser. No. 06/482,999, filed Mar. 11, 1983, each of which is now abandoned, and this application corresponds to British patent application Nos. 8121699, filed Jul. 15, 1981 and 8135738, filed Nov. 26, 1981, all of the above of which are incorporated herein by reference.

This invention relates to the field of recombinant DNA biotechnology. In particular it relates to the use of recombinant DNA biotechnology in the production of human calcitonin precursor structural gene, the insertion of said gene in a vector system, the cloning thereof and subsequently the production of human calcitonin.

Calcitonin is a small polypeptide hormone consisting of 32 amino acid residues (3500 mol. wt) synthesized and secreted in humans by the C-cells of the thyroid gland.

The main physiological function of calcitonin is to limit skeletal breakdown during times of calcium and phosphorus requirement, for example during growth, pregnancy and lactation. Thus for instance the absence of calcitonin during rapid growth in adolescence causes bone loss. A similar loss of bone may occur in pregnancy, when calcitonin secretion is absent. Calcitonin levels in men are higher than in women, and in both sexes, levels decline with age. This is particularly apparent in women after the menopause, where low levels of calcitonin appear to be an important factor in post-menopausal bone loss and osteoporosis. It is probable that should human calcitonin become commercially available in sufficient quantity, the peptide will be used alone or in combination with other drugs in the prevention and treatment of post-menopausal osteoporosis. Calcitonin may also be helpful in the treatment of elevated plasma calcium due to malignant deposits in bone. The commonest cause of this is cancer in the breast with secondary deposits in the skeleton. The action here probably reflects in part inhibitory action of calcitonin in osteoclasts. The latter are partly responsible for increased bone destruction leading in turn to elevated plasma calcium levels. Calcitonin may also have a direct action on cancer cells in bone and thus may play a role in the action of calcitonin in lowering elevated plasma calcium levels due to malignant deposits in bone.

At present, calcitonin (purified from salmon) is used in pharmacological rather than replacement doses, for the treatment of Paget's disease. This is a common condition affecting, in the main, people over 40 years of age. In this group as many as 4% of the population may be affected. Thus in the U.K., for instance, although the disease is usually asymptomatic, there are tens of thousands of people needing treatment. Unfortunately prolonged treatment with salmon calcitonin has proved impracticable due to immunological rejection of the fish calcitonin variant in about 25% of cases. Consequently there is already a need for large amounts of human calcitonin.

BRIEF DESCRIPTION OF THE DRAWINGS

FIGS. 1A, 1B, and 1C depict the mRNA directed cell-free protein synthesis of human calcitonin precursor polyproteins.

FIG. 4A depicts the nucleotide sequence of the human calcitonin precursor polyprotein structural gene and the amino acids it encodes.

We have elucidated the fine structure of a human calcitonin structural gene, which may be inserted into a prokaryote or eukaryote cell system by known recombinant DNA techniques, such that human calcitonin, in addition to other peptides encoded within the structural gene, may be synthesised in large quantities, purified, and subsequently used for pharmacological purposes.

Total human poly(A)-containing mRNA isolated from a medullary carcinoma of the thyroid directs the synthesis in cell-free protein synthesizing systems of a major polypeptide of estimated mol. wt. 21000. This, and a series of minor polypeptides of lesser abundance are precipitable with antiserum raised against synthetic human calcitonin. The experiments conducted to show this are described hereinafter and the results (shown in FIG. 1) contrast markedly with the known mol. wt. of calcitonin circulating in normal human serum (3500).

Analysis of the mRNA species which direct the synthesis of these high molecular weight presumptive calcitonin precursors, was carried out by a combination of recombinant DNA technology, DNA sequence analysis, and size determination of the calcitonin mRNA. Thus total poly(A)-containing RNA known to direct the synthesis of high molecular weight immunoprecipitable forms of human calcitonin, was used as a template to synthesize a double-stranded cDNA population. This was inserted into plasmid DNA using established procedures and transformed into a suitable E. coli host. Colonies containing cDNA sequences representative of the most abundant thyroid poly(A)-containing RNA populations were selected using in situ hybridisation procedures, and those containing calcitonin cDNA sequence then identified by hybridisation translation. We also describe here the detailed analysis of two of these plasmids designated phT-B3 and phT-B6, and their subsequent use to determine the size, sequence and coding potential of those mRNA(s) encoded by the calcitonin structural gene(s).

Figure 2A:
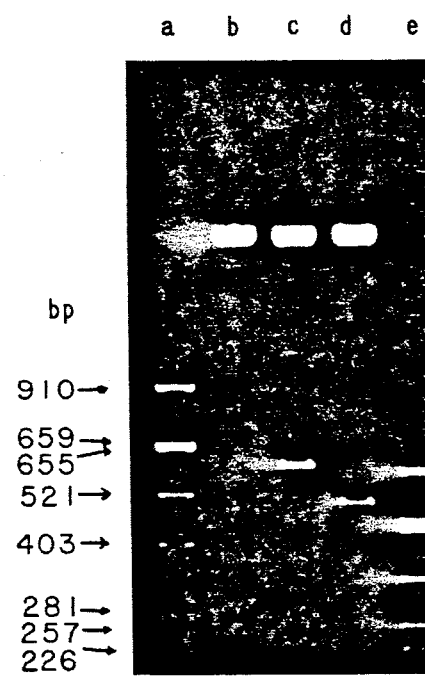
FIGS. 2A, 2B, and 2C depict the characterization of plasmids containing human calcitonin precursor polyprotein cDNA sequences.

The results depicted in FIG. 2 demonstrate:

(A) That the recombinant plasmids contain additional DNA sequence (phT-B6, 490 bps; phT-B3, 590 bps) when compared with the parental plasmid DNA, as determined by restriction analysis using the endonuclease Pst I.

(B) That both recombinant plasmids contain sequences capable of hybridising a thyroid mRNA species which directs the synthesis of the presumptive human calcitonin precursor polyprotein in a cell-free protein synthesizing system.

(C) That both recombinant plasmids contain cDNA sequence in common as judged by restriction endonuclease mapping, but that phT-B3 contains additional sequence at one end of a common fragment, and phT-B6 additional sequence at the other.

Figure 3:
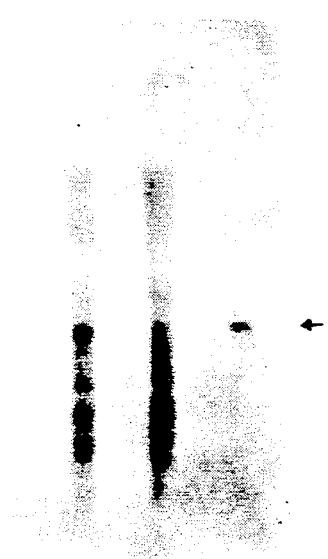
FIG. 3 depicts a size estimation of human calcitonin precursor polyprotein mRNA.

FIG. 3 shows the results of an RNA blotting experiment using a $^{32}$P-labelled phT-B3 hybridisation probe. From this it is apparent that the mRNA species in question are present in large amounts in thyroid tissue and are 1000±100 nucleotides in length. That data described above defines the source of calcitonin mRNA, the size of the mRNA and demonstrates that calcitonin is synthesized as a high molecular weight precursor polyprotein which in vivo must require extensive post-translational processing prior to secretion.

DNA sequence analysis of the cloned cDNA sequences (i) defines the relative position of the calcitonin peptide within this precursor polyprotein.

Figure 4B:
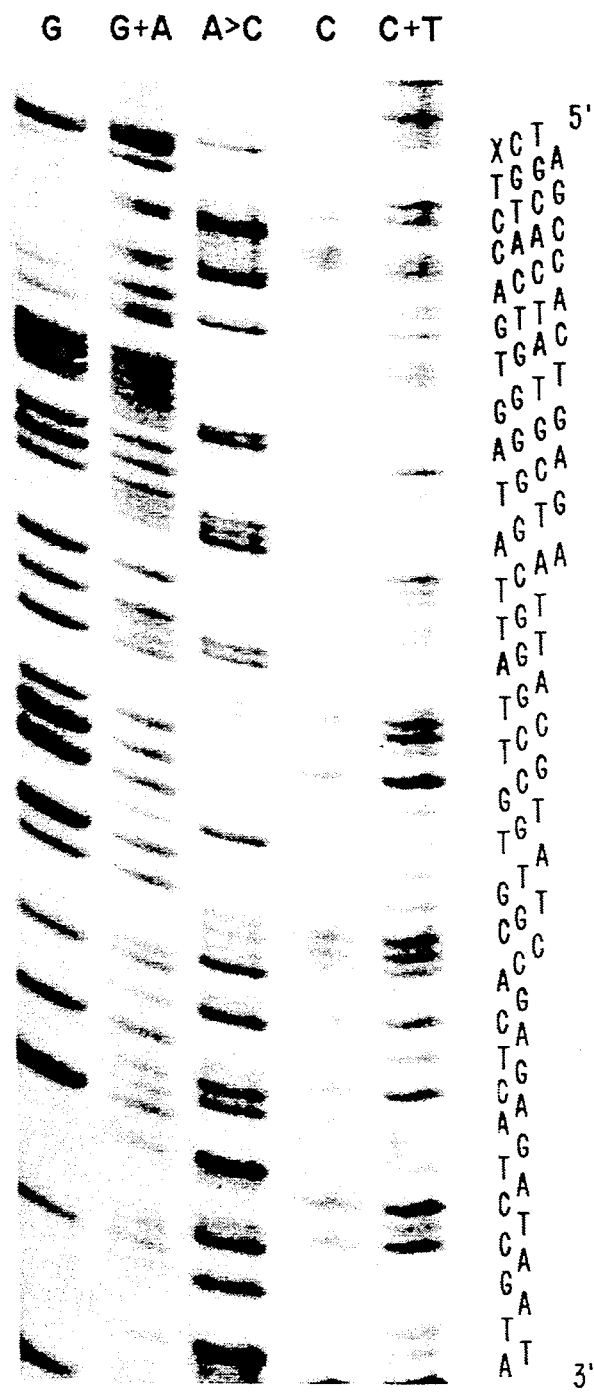
FIG. 4B depicts a portion of that sequence.
Figure 5:
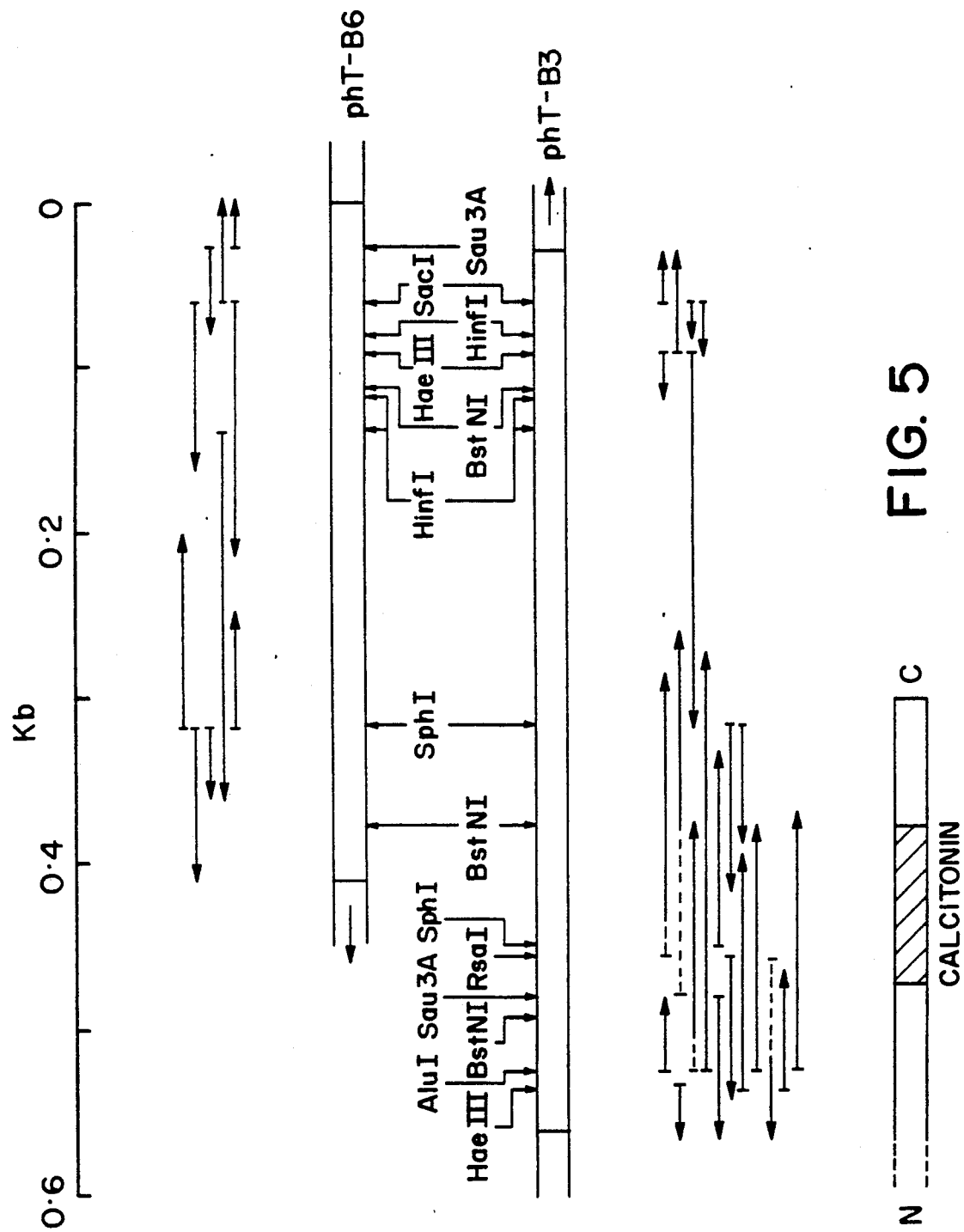
FIG. 5 schematically depicts the sequencing strategy used to obtain the DNA sequence in FIG. 4A.

(ii) reveals the amino acid sequence of the flanking NH$_2$-terminal and COOH-terminal peptides. FIG. 4 depicts the nucleotide sequence of cDNA inserted into plasmids phT-B3 and phT-B6 and FIG. 5 depicts the DNA sequencing strategy employed to determine this sequence. One (phT-B6) contains the whole of the 3' untranslated region of the mRNA, part of the sequence encoding the calcitonin peptide, and reveals that the mRNA encodes a further 25 amino acids after the COOH-terminal proline of calcitonin before a stop codon is encountered in phase. The other (phT-B3) contains a sequence which specifies the whole of the calcitonin peptide, the additional 25 amino acids of the flanking COOH-terminal (cryptic) peptide, a 36 amino acid NH$_2$-terminal (cryptic) flanking peptide, and most of the 3' untranslated region of the mRNA. In all we have sequenced 580 bases or 60% of the total human calcitonin mRNA using two overlapping cDNA clones.

The human calcitonin structural gene(s) encode mRNA species of 1000±100 bases in length. Translation of these mRNAs gives rise to a 21,000 mol. wt. precursor polyprotein. The calcitonin peptide resides towards the COOH-terminus of this polyprotein, flanked on the COOH-terminal side by an additional 25 amino acids, and on the NH$_2$-terminal side by an amino-acid sequence of as yet undetermined length through greater than 36 amino acids in length.

Thus, in one aspect the present invention comprises human calcitonin precursor polyprotein structural gene.

The invention also comprises a DNA transfer vector, especially a plasmid, having an inserted polypeptide fragment including the following amino acid sequence:

—cys—gly—asn—leu—ser—thr—cys—met—leu—gly—thr—
—tyr—thr—gln—asp—phe—asn—lys—phe—his—thr—phe—
—pro—gln—thr—ala—ile—gly—val—gly—ala—pro.

The invention also includes DNA transfer vector, especially a plasmid, having an inserted polypeptide fragment which includes the following amino acid sequence:

—val—leu—leu—ala—ala—leu—val—gln—asp—tyr—val—gln—met—
—lys—ala—ser—glu—leu—glu—gln—glu—gln—glu—arg—glu—gly—
—ser—ser—leu—asp—ser—pro—arg—ser—lys—arg—
—cys—gly—asn—leu—ser—thr—cys—met—leu—gly—thr—

Further according to the invention a method of forming a DNA transfer vector having a nucleotide sequence coding for a polypeptide comprising the amino acid sequence of human calcitonin comprises (i) providing mRNA coding for a polypeptide comprising the amino acid sequence of human calcitonin, (ii) synthesizing a double stranded cDNA one strand of which has a nucleotide sequence complementary to that of the mRNA, and (iii) inserting said double stranded cDNA in a DNA transfer vector.

The mRNA is suitably provided by cells containing the mRNA originating from the thyroid gland of a calcitonin-producing organism. Other sources of such cells include the lung and brain.

The DNA transfer vector is suitably transferred to and replicated in a microorganism strain, e.g. a bacterium such as *Escherichis coli.*

The invention also provides a polypeptide containing the amino acid sequence of human calcitonin which is processable, suitably by cleaving, to produce human calcitonin. Such polypeptide is suitably a fusion protein comprising a host protein in combination with a peptide comprising the amino acid sequence of human calcitonin.

The invention still further provides a method for the production of human calcitonin comprising processing a polypeptide to produce human calcitonin in which said polypeptide has been expressed by a host organism which has been transformed with a gene-containing DNA transfer vector comprising an inserted gene encoding a polypeptide comprising the amino acid sequence of human calcitonin. undertaken construct and characterise plasmids containing complementary DNA sequences to human calcitonin precursor polyprotein, and the subsequent production of human calcitonin from trp [-calcitonin fusion proteins.

I. MATERIALS AND METHODS a. Materials

Restriction enzyme PstI was obtained from Boehringer and calf thymus terminal deoxynucleotidyl transferase from P.L. Biochemicals. All other enzymes were obtained from sources described previously (Craig R. K. Hall, L. Parker, D. & Campbell, P. N. (1981) Biochem. J. 194, 989-998). L-[$^{35}$S]-methionine (700-1300

Ci/mmol), deoxy[5-³H]cytidine 5'-triphosphate (18.4 Ci/mmol), deoxy[8-³H]guanosine 5'-triphosphate (11.7 Ci/mmol), adenosine 5'-[γ-³²P]triphosphate (2000–3000 Ci/mmol) and deoxyguanosine 5'-[α-³²P]triphosphate (≧400 Ci/mmol) were from Amersham International; AMV reverse transcriptase (lot no. G-91180) was provided by Dr. J. W. Beard, Life Sciences Inc., St. Petersburg, Fla. 33707, U.S.A. All other chemicals and solvents were obtained from sources previously described (Craig, R. K., Brown, P. A., Harrison O. S. McIlreavy, D. & Campbell, P. N. (1976) Biochem. J. 160, 57–74 Craig, R. K. Boulton, A. P. Harrison, O. S. Parker, D. & Campbell, P. N. (1979) Biochem. J. 181, 737–756); (Pascall, J. C. Boulton, A. P. Parker, D., Hall, L. & Craig, R. K. (1981) Biochem. J. 196, 567–574).

b. Isolation of poly(A)-containing RNA from human medullary carcinoma of the thyroid: the construction, transformation and selection of recombinant plasmids Total RNA was isolated from frozen human thyroid medullary carcinoma tissue as described by (Hall, L. Craig, R. K. & Campbell, P. N. (1979) Nature (London) 277, 54–56), and residual DNA removed by digestion with deoxyribonuclease as described by Zimmerman, S. B. and Sandeen G. (1966) Anal. Biochem. 14, 269–277. Poly (A)-containing RNA was then isolated by affinity chromatography on oligo-(dT)-cellulose, and a size-selected double-stranded cDNA population was then synthesized from the resulting poly(A)-containing RNA population as described previously (Craig et al., 1981; Hall, L. Davies, M. S. & Craig, R. K. (1981) Nucleic Acids Res. 9, 65–84). The size-selected double-stranded cDNA was then extended at the 3'-hydroxyl termini with dC residues in the following manner. Double-stranded cDNA (1 μg/ml was dissolved in 30 mM-Tris/100 mM-cacodylic acid (adjusted to pH 7.5 with 10 m-KOH) containing 2 mM-CoCl₂, 0.1 mM-dithiothreitol, 50 μg of nuclease-free bovine serum albumin/ml, and 0.1 mM-[³H] dCTP (4 Ci/mmol). Terminal deoxynucleotidyl transferase (300 units/ml) was then added and the mixture incubated at 30° C. When a 30–50 residue long poly(dC)tail had been added (approx. 15 min as determined by trichloroacetic acid precipitation of 1 μl amounts at 5 min intervals), the reaction was terminated by extraction with phenol/chloroform, and the nucleic acid was recovered by ethanol precipitation. The precipitate was washed twice with ethanol, dissolved in double-distilled water and stored at −70° C.

Highly purified supercoiled pAT153 DNA prepared as described previously (Craig et al., 1981) was digested with the restriction endonuclease PstI, then tailed with poly(dG)₁₂ essentially as described above, except that the DNA was present at 50 μg/ml. [³H]dGTP (1.7 Ci/mmol) replaced dCTP as the radiolabelled deoxynucleotide triphosphate, and terminal deoxynucleotidyl transferase was present at a final concentration of 800 units/ml. Poly(dC)-tailed cDNA and poly(dG)-tailed pAT153 DNA were then annealed in 10 mμ-Tris/HCl, pH 7.6, containing 200 mM-NaCl and 1 mM-EDTA, in polypropylene 0.4 ml "snap-cap" tubes at a final concentration of 0.4 μg/ml and 4 μg/ml respectively. The mixture was heated in a water bath to 70° C. for 30 min, the water bath switched off, and the hybridization mixture allowed to cool to room temperature overnight. The amount of poly(dC)-tailed cDNA used for transformation varied from 10 to 20 ng.

The resulting chimaeric plasmid DNA was then used to transform *Escherichia coli* HB101 HB101 rec A⁻. (Boyer, H. W. & Roulland-Dussoix, D. (1969) J. Mol. Biol. 41, 459–472), under conditions of good microbiological practice in accordance with the guidelines laid down by the British Genetic Manipulation Advisory Group, using methodology described elsewhere (Craig et al., 1981). Transformed cells were selected on 1.5% (w/v) agar in L-broth containing 12.5 μg of tetracycline/ml. Individual colonies were then replica plated onto fresh agar plates containing 12.5 μg of tetracycline/ml alone or 100 μg of ampicillin/ml alone. Those colonies found to be sensitive to ampicillin were selected for subsequent experimentation.

c. Identification of plasmids containing human calcitonin precursor polyprotein cDNA sequences, and characterization of calcitonin precursor polyprotein mRNA.

Colony filter hybridization in situ, plasmid growth and purification, positive hybridization-translation, purification of individual cDNA sequences, and size estimation of individual mRNA sequences using the "Northern" transfer technique have been described elsewhere (see Craig et al., 1981; Burditt, I. J. Parker, D. Craig, R. K. Getova, T. & Campbell, P. N. (1981)Biochem, J. 194 999–1006; Hall et al., 1981). Nick-translation of plasmids was as described by Rigby, P. W. J. Dieckmann, M. Rhodes, C. & Berg. P. (1977) J. Mol. Biol. 113, 237–251). Unless specifically stated otherwise all restriction enzyme analyses were performed using the ionic conditions recommended by the manufacturers. Size analysis of restricted plasmid DNA was performed by electrophoresis on flat-bed agarose gels as described elsewhere (Craig et al., 1981).

d. Cell-free protein synthesis and product analysis.

mRNA-directed cell-free protein synthesis in the wheat-germ cell-free protein synthesizing system and antibody precipitation procedures were as described by Craig et al., (1976). SDS/polyacrylamide-gel electrophoretic analysis was performed using slab gels as described by Pascall et al. (1981). Fluorography followed the procedure of (Bonner, W. M. & Laskey, R. A. (1974) Eur. J. Biochem. 46, 83–88) except that dimethylsulphoxide was replaced by glacial acetic acid (Burckhardt, J. Telford, J. & Birnstiel, M. L. (1979) Nucleic Acids Res. 6, 2963–2971).

II. RESULTS e. Isolation and characterization of a poly(A)-containing RNA population from human medullary thyroid carcinoma tissue.

Total human poly(A)-containing RNA isolated from a medullary carcinoma of the thyroid was added to a wheat-germ cell-free protein synthesizing system, and the resulting [³⁵S]methionine-labelled proteins were analysed by SDS/polyacrylamide-gel electrophoresis and fluorography. The results (FIG. 1a) demonstrate that a spectrum of proteins up to mol. wt. 60000 was synthesized. The most prominent of these, a protein of estimated mol. wt. 21000, proved to be precipitable with antiserum raised against human calcitonin. In addition to this protein, three less abundant peptides of estimated mol. wt. 19500, 18000 and 15000 were also precipitated by calcitonin-specific antiserum. It is believed that these may represent partially processed calcitonin precursor polyproteins, a result of post-translational processing activities present in the wheat-germ cell-free extract (see Pascall et al. 1981). Alternatively these may result from the translation of multiple poly(A)-containing species encoding different polyproteins each containing the calcitonin amino acid sequence. These differences were particularly apparent at $Mg^{2+}$ concentrations which were suboptimal for protein synthesis. Thus at 1.5 mM-$Mg^{2+}$ the predominant polypeptide was the mol. wt. 18000 calcitonin precursor polyprotein form whilst at 2.5 mM-$Mg^{2+}$, the optimum for protein synthesis, the mol. wt. 21000 calcitonin precursor polyprotein form predominant (see FIG. 1b). Immaterial of the $Mg^{2+}$ concentration, the predominant polypeptides remained precipitable with antiserum raised against human calcitonin (FIG. 1c).

Overall, on the basis of the sources of tissue and the identification of polypeptide immunoprecipitable with human calcitonin antisera as the predominant products of mRNA-directed cell-free protein synthesis, we conclude that an abundant poly(A)-containing RNA species present in human thyroid medullary carcinoma tissue directs the synthesis of calcitonin precursor polyprotein(s).

f. Construction of recombinant cDNA plasmids using total poly(A)-containing RNA isolated from a human medullary carcinoma of the thyroid.

All manipulations followed the procedures outlined for the construction of recombinant plasmids containing human and guinea-pig milk protein cDNA sequences (see Craig et al., 1981; Hall et al., 1981) except where specifically stated in the Methods section using the overall strategy outlined in FIG. 6.

Briefly, cDNA representative of the total poly(A)-containing RNA population isolated from the human medullary carcinoma of the thyroid was synthesized by using AMV reverse transcriptase. Size analysis using agarose-gel electrophoresis showed that the bulk of the cDNA synthesized ranged in size from 500 to 1500 nucleotides in length. This was converted to a double-stranded form using AMV reverse transcriptase, followed by $S_1$ nuclease excision of the resultant hairpin loop. This population was then sized by preparative agarose-gel electrophoresis and those sequences ranging from 300 to 2500 nucleotides in length were eluted from the gel, and their 3'-hydroxyl termini extended with poly(dC)$_{50}$ using calf thymus terminal deoxynucleotidyl transferase. This population was then annealed with PstI-restricted pAT153 DNA which had previously been extended at the 3'-hydroxy termini with poly(dG)$_{12}$. The resulting chimaeric molecules were used to transform a rec $A^-$ strain of E.coli HB101 under conditions of good microbiological practice. Transformants were selected on L-agar plates containing tetracycline, and colonies containing recombinant plasmids were then selected by replica plating onto L-agar containing ampicillin alone, or tetracycline alone. In total a single transformation using 20 ng of double-stranded tailed cDNA yielded 107 colonies that had lost sensitivity to ampicillin, and therefore were presumed to contain cDNA sequences inserted at the PstI site of pAT153.

g. Identification and characterization of recombinant plasmids containing human calcitonin cDNA sequences.

It was apparent from cell-free protein synthesizing studies that the human medullary carcinoma of the thyroid poly(A)-containing RNA population contained an abundant mRNA population which directed the synthesis of calcitonin precursor polyprotein(s). Consequently total base-cleaved $^{32}$P-labelled poly(A)-containing RNA from human medullary carcinoma was used to identify, in a preliminary manner using in situ hybridization procedures, those colonies most likely to contain calcitonin precursor polyprotein cDNA sequences (see the Methods section). All the ampillin-sensitive colonies were screened in this manner, and 17 (16%) showed significant hybridization over the background. Of these, 11 were selected and grown in liquid culture, the plasmid DNA was isolated, and the presence of additional DNA sequence determined by digestion with the restriction endonuclease PstI, followed by agarose-gel electrophoresis. This confirmed that all but one contained additional DNA as compared with the parental plasmid pA153. The detailed characterization of two plasmids, phT-B3 and phT-B6, is described.

Size analysis of the inserted cDNA sequences by agarose-gel electrophoresis after excision of the cDNA by digestion with the restriction endonuclease PstI, showed (FIG. 2A) that phT-B3 and phT-B6 contained 590 and 490 base pairs of inserted sequence.

Figure 2B:
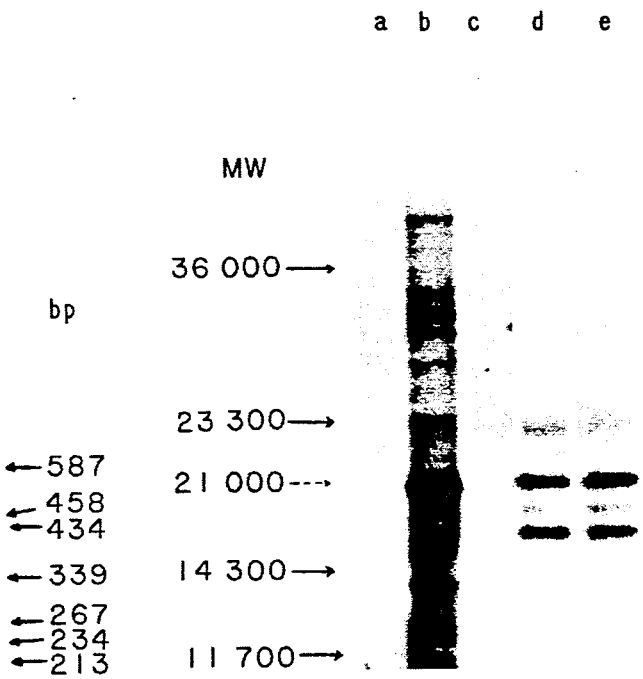
Figure 2C:
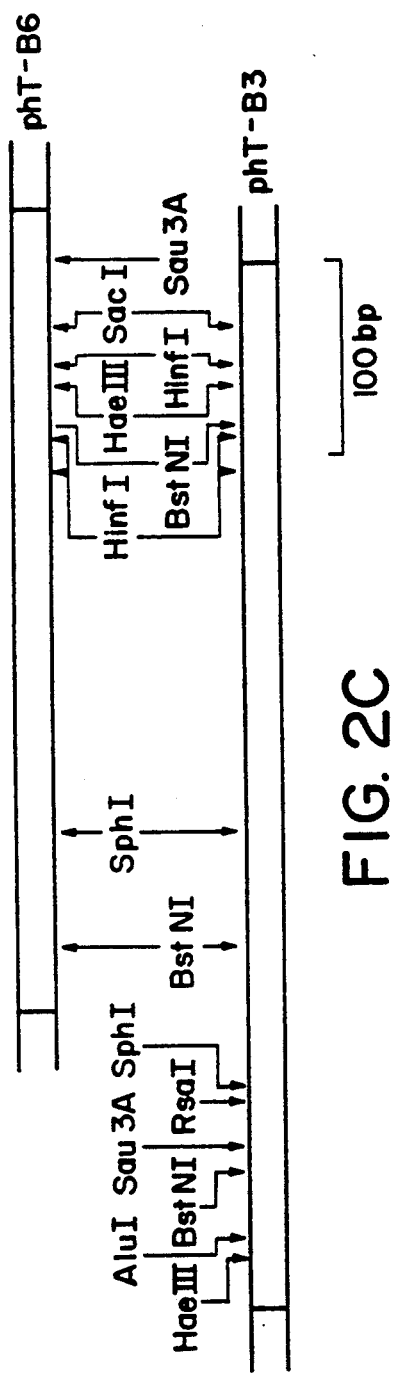

Identification of the coding sequences present in each plasmid was carried out by SDS/polyacrylamide-gel electrophoresis of the wheat-germ cell-free translation products of mRNA isolated by hybridization under stringent conditions to partially restricted denatured plasmid DNA immobilized on DBM-paper filters (see Craig et al., 1981). This demonstrated that both plasmids contained DNA sequences complementary to the medullary thyroid carcinoma mRNA species which directed the synthesis of the abundant calcitonin precursor protein (FIG. 2B). In each instance, although cell-free protein synthesis was performed in the presence of 2.5 mM-$Mg^{2+}$, both the 21000 and 18000 molecular weight calcitonin precursor polyprotein forms were present. Subsequent mapping of these sequences using a variety of restriction endonucleases (FIG. 2C) showed that both recombinant plasmids contained cDNA sequences in common, but that phT-B3 contained an additional sequence at one end of the common fragment and phT-B6 an additional sequence at the other.

To determine the proportion of the calcitonin precursor polyprotein mRNA sequence within the characterized recombinants, the size of the mRNA was estimated using RNA blotting techniques (Alwine, J. C. Kemp, D. J. & Stark, G. R. (1977) Proc. Natl. Acad. Sci. U.S.A. 74, 5350-5354) after separation of glyoxal-treated poly(A)-containing RNA (McMaster, G. K. & Carmichael, G. G. (1977) Proc. Natl. Acad. Sci. U.S.A. 74, 4835-4838) by horizontal agarose-gel electrophoresis (FIG. 3). This demonstrated that the human calcitonin precursor polyprotein mRNA was 1000±100 nucleotides in length. Thus the cDNA sequence inserted into phT-B3 and phT-B6 represented in total 60–65% of the mRNA sequence. A parallel analysis of the non-polyadenylated human thyroid medullary carcinoma RNA also revealed the presence of calcitonin precursor polyprotein mRNA of identical length, but also discrete bands of lower molecular weight, either partially degraded mRNA or discrete lower molecular weight mRNA species containing sequence in common with the defined calcitonin sequence (see FIG. 4). Calcitonin precursor polyprotein mRNA was not present in detectable amounts, under the conditions employed, in total poly(A)-containing RNA isolated from full-term human placental tissue, or from T-47D cells, a human cell line of mammary origin (see FIG. 3).

EXPLANATION OF FIGS. 1 TO 6 OF THE DRAWINGS

FIG. 1. mRNA directed cell-free protein synthesis of human calcitonin precursor polyproteins as judged by immunoprecipitation and SDS/polyacrylamide-gel electrophoresis.

Total poly(A)-containing RNA (0.2 µg/assay) isolated from frozen human thyroid medullary carcinoma tissue (4 g) (see Hall et al., (1979) Nature (London) 277, 54–56) was added to a wheat-germ cell-free protein-synthesizing system and the resulting [$^{35}$S]methionine-labelled proteins were separated by using SDS/polyacrylamide-gel electrophoresis, then visualized using fluorography (see Materials and methods above). (A) Lane (i), no added mRNA; lane (ii), human thyroid medullary carcinoma poly(A)-containing RNA; lane (iii), as in lane (ii) but proteins were precipitated using antiserum raised against synthetic human calcitonin. (B) Lanes (i), (iii), (v) and (vii), human thyroid medullary carcinoma poly(A)-containing RNA translated at $Mg^{2+}$ concns. of 1.5, 2.0, 2.25 and 2.5 mM respectively. Lanes (ii), (iv), (vi) and (viii), no added RNA at $Mg^{2+}$ concns. of 1.5, 2.0, 2.25 and 2.5 mM respectively. (C) Lanes (i) and (iii), human thyroid medullary carcinoma poly(A)-containing RNA translated at $Mg^{2+}$ concns. of 1.5 and 2.5 mM respectively; lanes (ii) and (iv), as in lanes (i) and (iii) respectively, but proteins precipitated using antiserum raised against synthetic human calcitonin. Arrows represent the relative mobility of the following Coomassie Blue stained marker proteins of known molecular weight, (see Weber et al., 1972); glyceraldehyde-3-phosphate dehydrogenase (36000); tryspin (23300); and lysozyme (14309).

FIG. 2. Characterization of plasmids containing human calcitonin precursor polyprotein cDNA sequences. (A) Size analysis of inserted cDNA sequences. Plasmid DNA samples (0.25 µg) were digested with restriction endonucleases, then electropheresed on a 1.6% (w/v) agarose-gel as described previously (see Hall et al., 1981). DNA fragments of known size (see Sutcliffe, J. G. (978a) Cold Spring Harb. Symp. Quant. Biol. 43, 77–90; Sutcliffe, J. G. (1978b) Nucleic Acids Res. 5, 2721–2728) were generated by AluI digestion of pBR322 DNA and HaeIII digestion of pAT153 DNA.- Lane (a), AluI markers of 910, 659, 655, 521, 403, 281, 257 and 226 base pairs; lane (b), pAT153 DNA digested with PstI; lane (c), phT-B3 DNA digested with PstI; lane (d) phT-B6 DNA digested with PstI; lane (e), HaeIII markers of 587, 458, 434, 339, 267, 234 and 213 base pairs. (B) Positive hybridization translation. Sequence-specific poly(A)-containing RNA isolated by hybridization to partially restricted, denatured recombinant DNA immobilized on DBM-paper was added to a wheat-germ cell-free system and the [$^{35}$S]methionine-labelled cell-free translation products were separated by SDS/polyacrylamide-gel electrophoresis, then visualized by fluorography. Lane (a), no added RNA; lane (b), total human thyroid medullary carcinoma poly(A)-containing RNA; lanes (c), (d) and (e), poly(A)-containing RNA isolated by hybridization to plasmids pAT153, phT-B3 and phT-B6 respectively. Arrows denote the relative position of marker proteins as described in relation to FIG. 1, but in addition include cytochrome-C (11700). (c) Comparative restriction endonuclease maps of the inserted cDNA sequence within recombinant plasmids phT-B3 and phT-B6.

FIG. 3. Size estimation of human calcitonin precursor polyprotein mRNA.

RNA samples were treated with glyoxal, then loaded onto separate slots on a 1.5% (w/v) agarose-gel, electrophoresed and then blotted onto DBM-paper as described previously (Craig et al., 1981). The position of the human calcitonin precursor polyprotein mRNA sequence (arrowed) was determined by hybridization to a $^{32}$P-labelled nick-translated phT-B3 plasmid DNA hybridization probe ($5.6 \times 10^7$ c.p.m./µg). Lane (i), T-47D poly(A)-containing RNA (1 µg); lane (ii), human placental poly(A)-containing RNA (1 µg); lane (iii), total human thyroid medullary carcinoma RNA (40 µg); lane (iv), non-polyadenylated human thyroid medullary carcinoma RNA (40 µg); lane (v), human thyroid medullary carcinoma total poly-(A)-containing RNA (1 µg). Size estimations were determined by direct comparisons with the mobilities of glyoxal-treated linear pBR322 DNA (4362 bases), rabbit reticulocyte 18S RNA (2060 bases), a BamHI/PstI digest of pBR322 DNA (3237 and 1125 bases), and E. coli tRNA (80 bases).

As described above, FIG. 4 shows the nucleotide sequence of the human calcitonin precursor polyprotein structural gene and the amino acids it encodes. The amino acids labelled 1–32 correspond to the previously known amino acid sequence of human calcitonin.

The amino acid sequence −1 to −36 represents the previously unknown cryptic $NH_2$-terminal flanking peptide, and the amino acid sequence +1 to +25 the cryptic carboxyl-terminal flanking peptide. Arrows define the region of nucleotide sequence which may be deduced from the adjacent DNA sequencing ladder. Boxed amino acids (−2 and −1; +1 to +4) represent predicted sites for proteolytic processing in vivo (see Steiner D. F., Quinn, P. S. Chan. S. J. Marsh J. and Tager H. S. (1980) Ann. N.Y. Acad. Sci. 343, 1–16). The glycine residue (+1), an important consideration in the construction of the expression vectors described below, is in vivo required during processing events for the amidation of the adjacent carboxyl terminal amino acids (Kreil, G., Suchanek, G. and Kindas-Mugge, 1. (1977) Fedn. Proc. 36, 2081–2086). Thus in human calcitonin glycine +1 is required for the amidation of the carboxyl-terminal proline residue (32), a feature required for biological activity.

FIG. 5 defines the nucleotide sequencing strategy carried out using the chemical cleavage procedure of Maxam A. M. and Gilbert W. Procn. Natn. Acad. Sci. U.S.A. 74 560–564 (1977).

Figure 6:
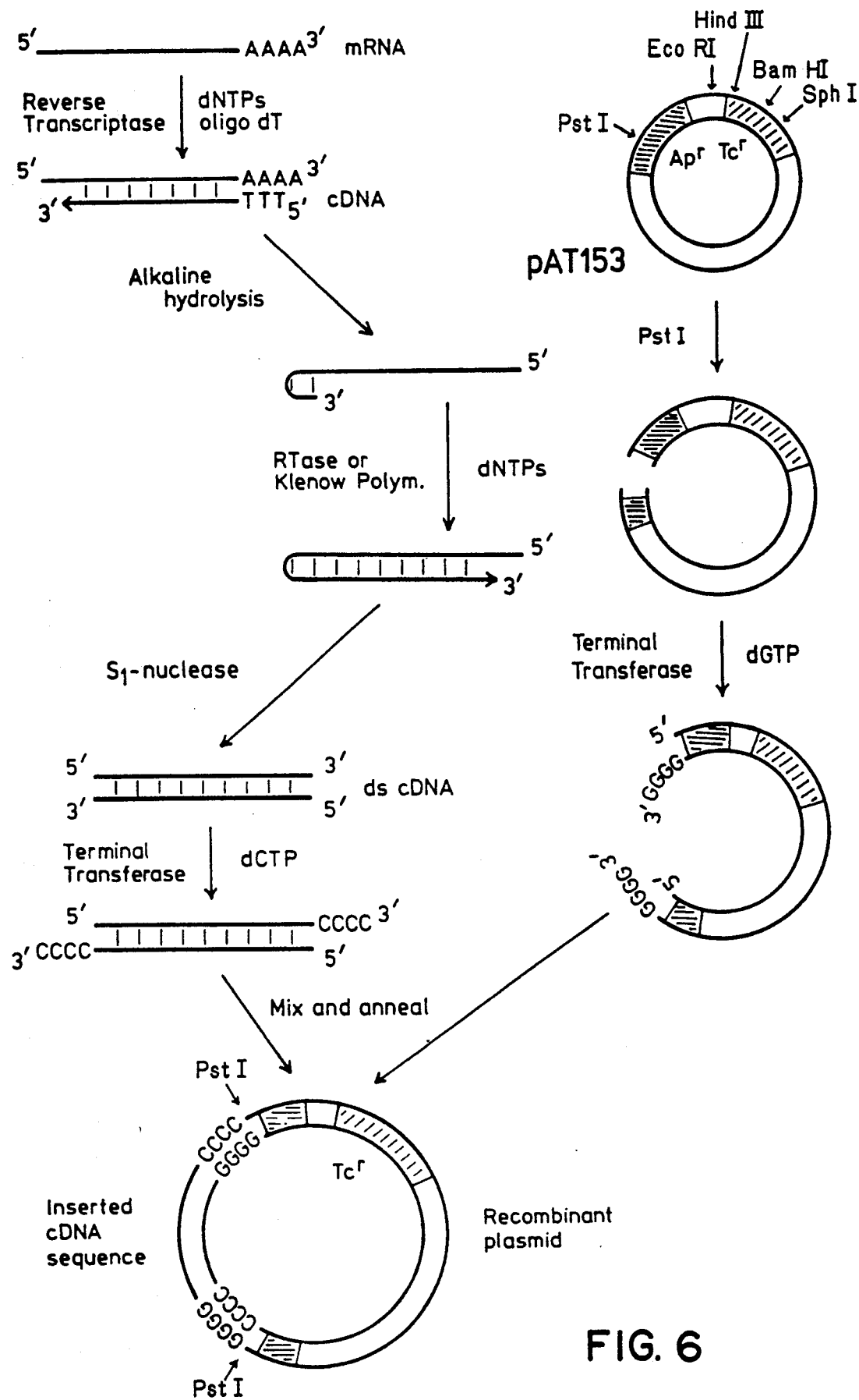
FIG. 6 schematically depicts the strategy for cloning of the human calcitonin precursor cDNA.

FIG. 6 depicts the overall cloning strategy.

There now follows a description of the production, using the expression vector designated pOT37, the combination therewith of the human calcitonin sequence derived from plasmid phT-B3 to produce a fusion protein, and the production therefrom of either human calcitonin or human calcitonin with an additional glycine residue at the carboxy-terminal end.

ISOLATION OF THE TRYPTOPHAN PROMOTER AND TRP E GENE

The tryptophan operon has been the subject of much attention in recent years. The result of this is the elucidation of the complete nucleotide sequence of the five structural genes and their control regions (C. Yanofsky et al Nucleic Acids Res 9, 6647–6668, 1981). The control regions and parts of the structural genes have also been used to construct vectors for the expression of foreign genes (B. E. Enger-Valk et al Gene 9, 69–85, 1980; W. Tacon, N. Carey and J. S. Emtage, Molec Cen Genet 177, 427–438, 1980; R. A. Hallewell and J. S. Emtage, Gene 9, 27–47, 1980). Earlier work had also shown that the control regions and the complete trp E gene could be isolated from the E coli chromosome on a Hind III fragment of ≃5700 bp (A. S. Hopkins, N. E. Murray and W. J. Brammar J Mol Biol 107, 549–569, 1976). The E coli operon has also been isolated from the DNA of trp transducing strains of phages Φ80 and λ (B. E. Enger-Valk et al loc cit).

Alternatively, the control region and trp E gene can be isolated using cosmid vectors and in vitro packaging (B. Hohn and K. Murray Proc Natl Acad Sci USA 74, 3259–3262, 1977; Collins, J. and Hohn, B. Proc Natl Acad Sci USA 75, 4242–4246, 1978). Thus, E coli chromosomal DNA was partially digested with Sau 3A and the resulting fragments ligated to the 10.3 kb cosmid 3030 that had previously been digested to completion with Bam HI. The cosmid 3030 contains a unique site for Bam HI and confers resistance to ampicillin. After ligation, the mixture was packaged in vitro and used to infect a trp E⁻ strain of E coli K12. Recombinants were selected on L-agar plates containing ampicillin from which they were replica plated onto M9 salts, glucose, casamino acids minimal agar plates supplemented with ampicillin. Recombinants were thus selected that complemented the trp E⁻ strain by their ability to grow in the absence of tryptophan. Several recombinants were identified and plasmid DNA isolated and characterised by restriction enzyme analysis. One cosmid, designated 3030/trp, producing a 5700 bp fragment on digestion with Hind III was selected for further use.

Cosmid 3030/trp was digested with Hind III, the fragments separated by agarose gel electrophoresis and the 5700 bp fragment recovered from a gel slice. Finally, this 5700 bp fragment was cloned into the Hind III site of pAT153 to produce the plasmid ptrp $E_{5700}$.

CONSTRUCTION OF pCT12

Figure 7:
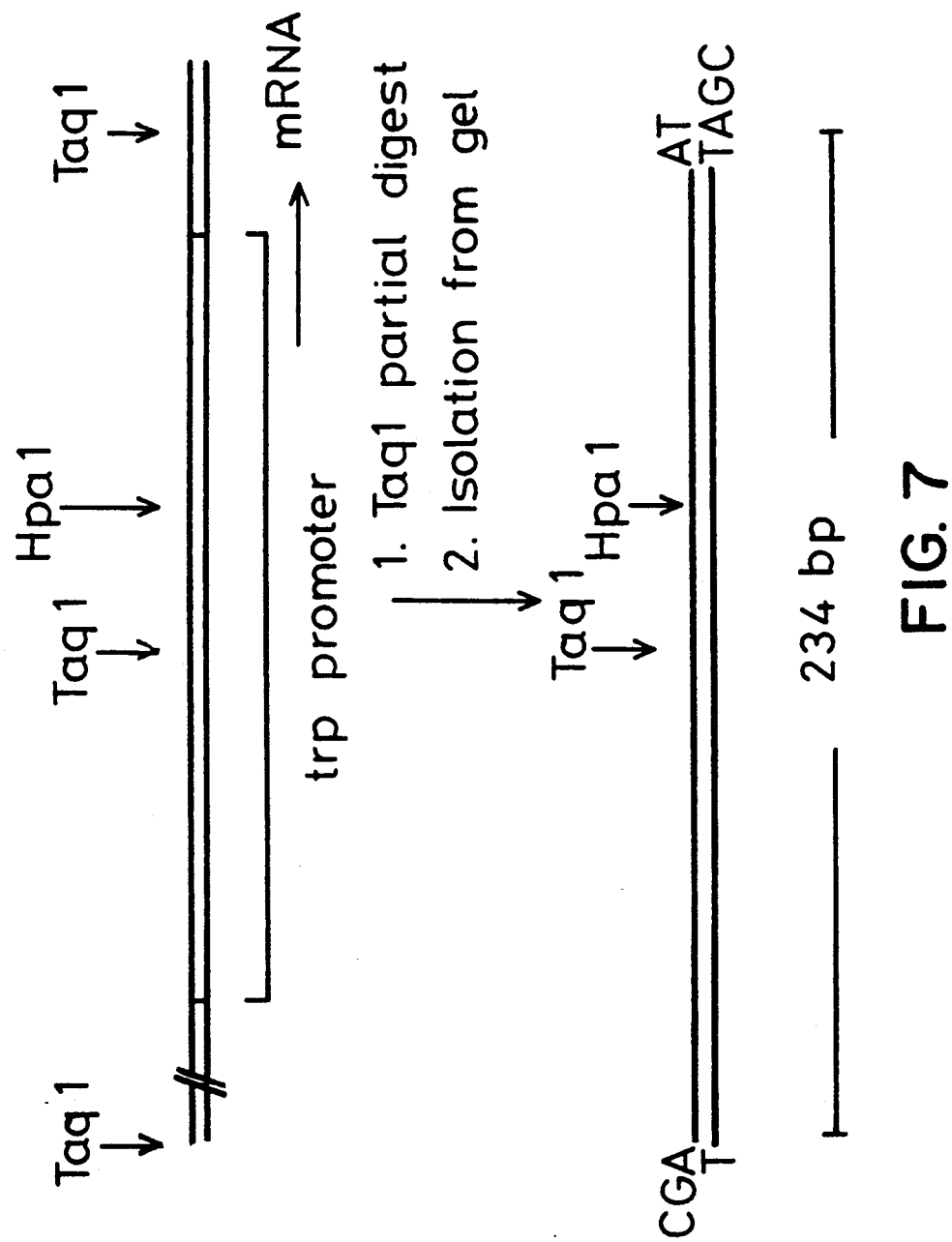
FIG. 7 schematically depicts a DNA fragment containing the bacterial trp promoter.

A schematic representation of a portion of the tryptophan promoter-containing fragment is given in FIG. 7. From this figure it can be seen that the complete tryptophan promoter-operator complex can be isolated on a Taq I restriction fragment of 234 base pairs (bp) if the DNA is digested under conditions where about 50% of the available sites are cleaved. Thus, 10 μg of ptrp $E_{5700}$ was incubated in 10 mM Tris-HCl pH 8.4, 100 mM NaCl, 6 mM MgCl$_2$ and 6 mM β-mercaptoethanol at 65° C. for 20 minutes with 4 units of Taq I. After incubation the reaction mixture was extracted with phenol, precipitated with ethanol, dissolved in water and electrophoresed on a 5% polyacrylamide gel. After electrophoresis the gel was stained with ethidium bromide and the 234 bp DNA band excised from the gel and the DNA recovered (A. M. Maxam and W. Gilbert, Proc Natl Acad Sci USA 74, 560–564, 1977).

This DNA fragment was then inserted into the Cla I site of the plasmid pAT153 (Twigg and Sherratt, Nature 283, 216, 1980). 10 μg of pAT153 was digested to completion with Cla I and the 5'-phosphate groups removed by incubation at 37° C. for 1 hour with 0.5 units of calf intestine alkaline phosphatase in 10 mM Tris-HCl, pH 8. This procedure prevents the plasmid recircularising in the absence of an inserted DNA fragment. 100 ng of the above treated pAT153 was ligated at 15° C. for 4 hours to 5 ng of the 234 bp DNA in a reaction containing 50 mM Tris-HCl pH 7.6, 10 mM MgCl$_2$, 20 mM dithiothreitol, 1 mM ATP and 20 units of T4 DNA ligase. The ligated DNA was then used to transform competent E coli K-12 strain HB101 (Boyer, H. W. and Roulland-Dussoix, D. J. Mol Biol 41, 459–472, 1969) by standard techniques (Hershfield, V. et al Proc Natl Acad Sci USA 71, 3455–3459, 1974) and the bacteria plated on L-agar plates containing 100 μg/ml ampicillin. Several ampicillin resistant colonies were selected, plasmid DNA prepared and the presence of the 234 bp fragment confirmed by restriction analysis.

Figure 8:
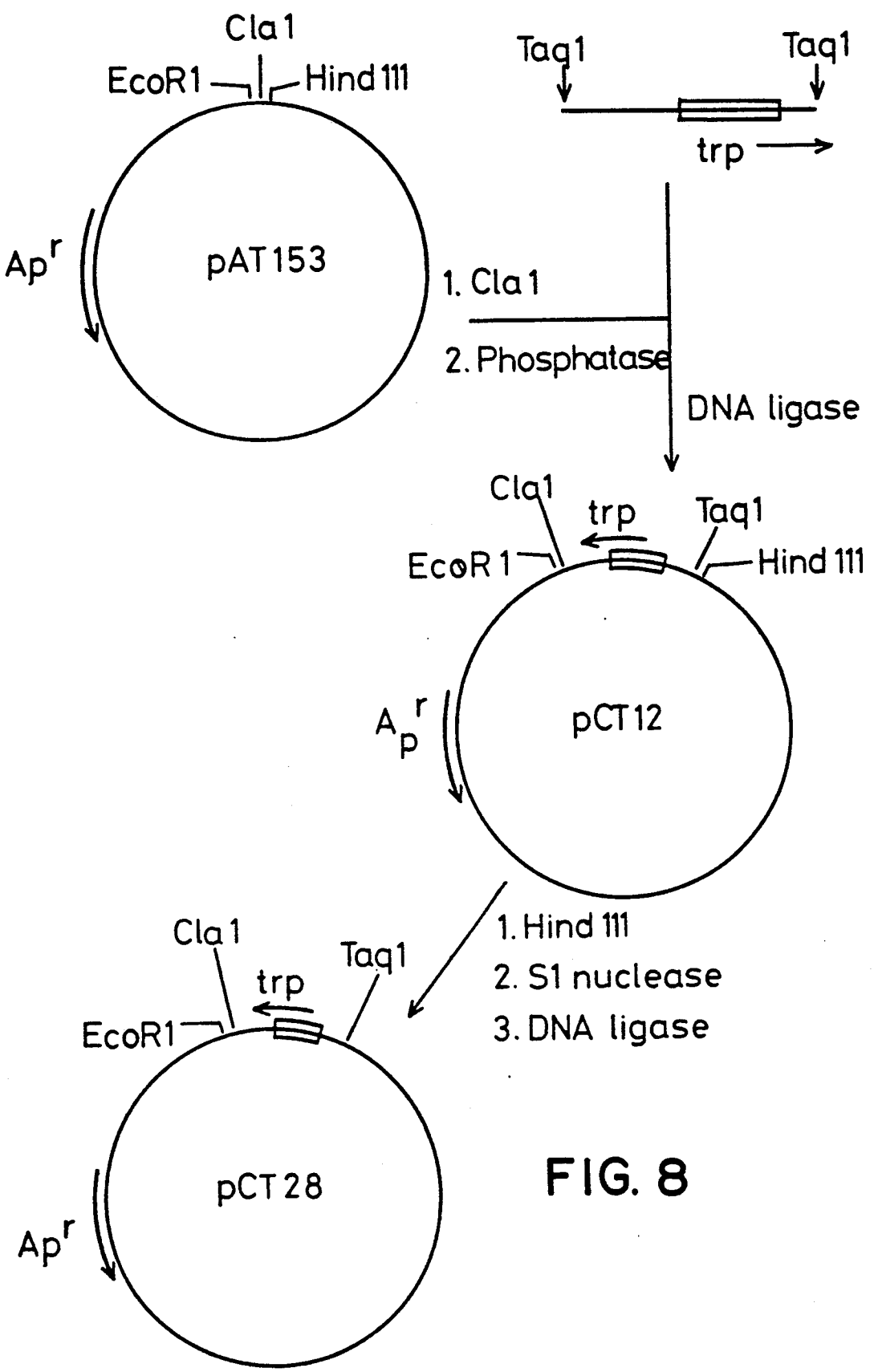
FIG. 8 schematically depicts the construction of plasmids pCT12 and pCT28.

The resulting plasmid, designated pCT12, has the structure shown in FIG. 8. It should be pointed out that insertion of the Taq fragment into the Cla I site reforms a Cla I site at the end downstream from the trp promoter.

MODIFICATION OF pCT12 pCT12 was further modified to produce pCT28 and pCT29 as follows. 2 μg of pCT12 was digested to completion with Hind III and then incubated at 20° C. for 30 minutes with 60 units of SI nuclease in a buffer containing 25 mM sodium acetate, pH 4.5, 0.3M NaCl and 1 mM zinc acetate to remove the protruding Hind III ends. The reaction was terminated by raising the pH to 7.6 and extracting the mixture with phenol/chloroform (1:1). The DNA was concentrated by ethanol precipitation and a sample incubated with T4 DNA ligase as described above and then used to transform E coli K12 strain HB101. Several ampicillin resistant clones were selected, plasmid DNA prepared and the absence of the Hind III site confirmed by restriction analysis. The resulting plasmid, designated pCT28, has the structure shown in FIG. 8.

pCT28 was further modified. 2 μg of EcoRI-digested pCT28 was incubated with 4 units of E coli DNA polymerase for 15 minutes at 10° C. in a reaction containing 50 mM Tris-HCl pH 7.6, 10 mM MgCl$_2$, 10 mM β-mercaptoethanol, 0.2 mM dATP and 0.2 mM dATP. After incubation the mixture was extracted with phenol, with chloroform and then ethanol precipitated. This treatment causes the 4 nucleotides complementary to the 5' protruding ends of the EcoRI site to be filled in:

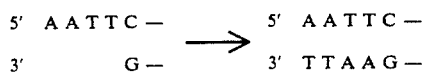

0.6 μg of the above treated pCT28 was treated with 50 units of T4 DNA ligase in the presence of 30 picomoles of the 5'-phosphorylated synthetic oligonucleotide pCCAAGCTTGG and in 10 μl T4 DNA ligase buffer at 25° C. for 16 hours. The mixture was then heated at 70° C. for 10 minutes to stop the reaction and the linkers cleaved by digestion with Hind III. The linear DNA, now with Hind III ends, was separated from the linkers by electrophoresis on an agarose gel from which it was subsequently recovered by electroelution and concentrated by ethanol precipitation. Ligation, followed by transformation of *E. coli* K-12 strain HB101, isolation of plasmid DNA and identification of plasmids with Hind III and EcoRI sites, produced the plasmid designated pCT29.

Figure 9:
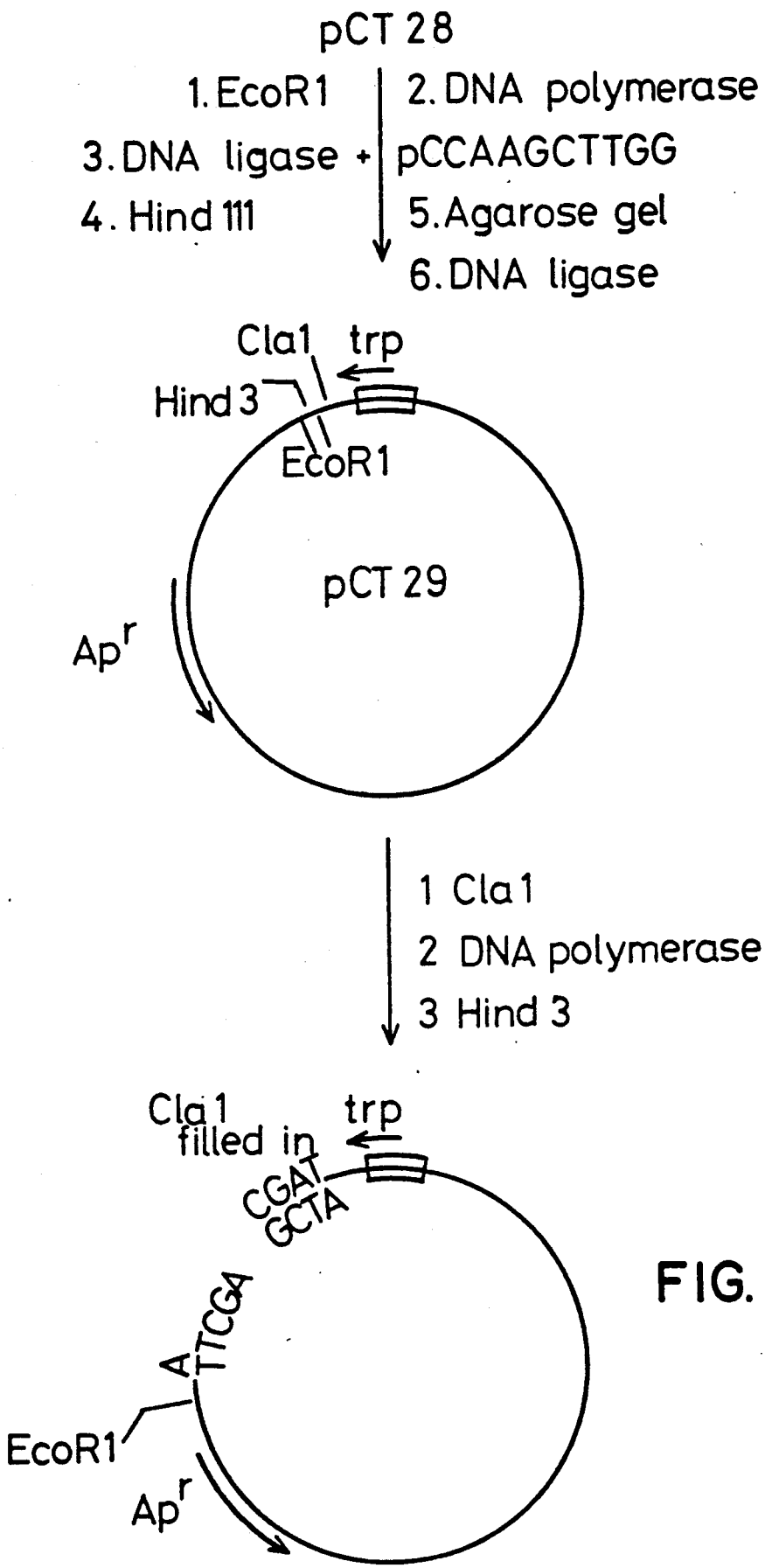
FIG. 9 schematically depicts the construction of plasmid pCT29.

PREPARATION OF pCT29 FOR CLONING TRP E GENE pCT29, FIG. 9, contains the *E. Coli* tryptophan promoter-operator region and, as well, unique restriction sites for the enzymes Cla I, Hind III and EcoRI downstream of the promoter region. Two of these sites, the Cla I and Hind III sites, were used to insert the trp E gene.

5 µg of pCT29 was cleaved with Cla I and the 5'-protruding ends filled in as described above using *E. coli* DNA polymerase in the presence of dCTP and dGTP. The polymerase reaction mixture was extracted with phenol, then with chloroform and the DNA finally precipitated with ethanol. The filled-in DNA was then digested with Hind III and the resulting fragments separated by agarose gel electrophoresis. The largest fragment was isolated from the gel by first staining with ethidium bromide, locating the DNA with ultraviolet light and cutting from the gel the portion of interest. The DNA was recovered from the gel fragment by electroelution and concentrated by ethanol precipitation.

ISOLATION OF THE TRP E GENE

Figure 10:
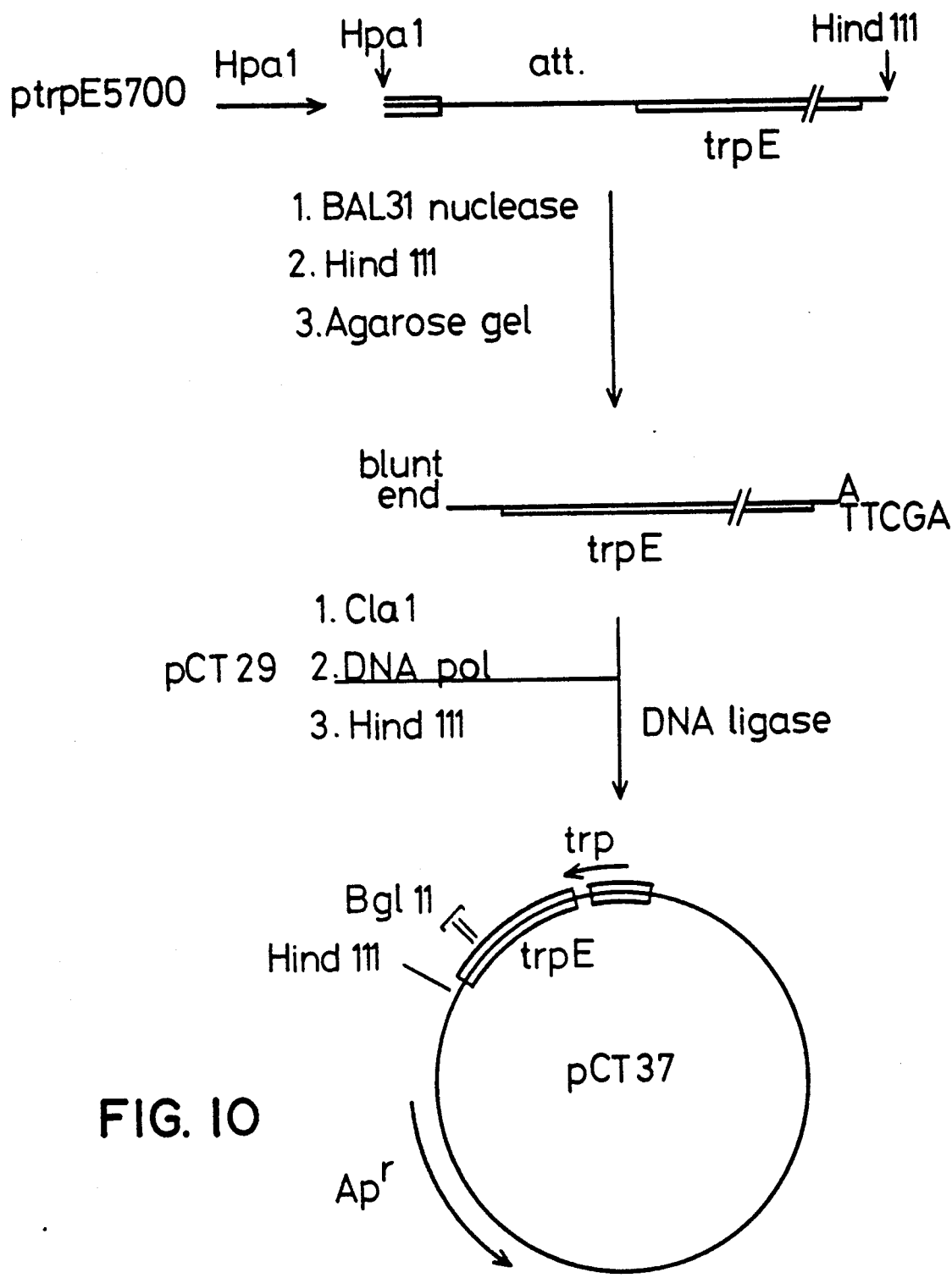
FIG. 10 schematically depicts the ligation reaction between the trp promoter fragment and pCT29.

The trp E gene is present on the plasmid ptrp $E_{5700}$, a portion of which is shown in FIG. 10. As described above however, ptrp $E_{5700}$ also contains the trp attenuator, a region concerned in the control of transcription from the trp attenuator as follows. To remove the attenuator region 5 µg of prtp $E_{5700}$ was digested with Hpa I and then treated with nuclease BAL 31. This nuclease is a highly specific nuclease that can be used to shorten DNA fragments from the ends. Further, its action produces blunt-ended molecules. 5 µg of Hpa I digested ptrp $E_{5700}$ was treated with 1.5 units of BAL 31 nuclease in 0.6M NaCl, 12 mM $MgCl_2$, 20 mM Tris-HCl pH 8, 1 mM EDTA at 30° C. for 1.5 minutes. The mixture was then phenol extracted, chloroform extracted and ethanol precipitated. This treatment removes 150-250 bp from each end of the DNA fragments and so will remove the attenuator region from most molecules as it is 150 bp from the Hpa I site. The above treated DNA fragments were digested to completion with Hind III and then separated by agarose gel electrophoresis. DNA containing the trp E gene was isolated from the gel by first staining the gel with ethidium bromide, locating the DNA with ultraviolet light and cutting from the gel DNA in the size range 1800–1850 bp. This DNA was recovered from the gel fragment by electroelution and concentrated by ethanol precipitation.

INSERTION OF THE TRP E GENE INTO pCT29

The trp E fragments isolated above can be inserted into pCT29 that had been modified as described above. FIG. 10 illustrates the ligation reaction. 0.2 µg of modified pCT29 and 80 ng of the trp E fragment were incubated at 20° C. for 16 hours with 100 units T4 DNA ligase in 50 mM Tris pH 7.6, 10 mM $MgCl_2$, 1 mM ATP and 20 mM dithiothreitol. The mixture was then used to transform *E coli* K12 strain HB101 as described above and transformants selected on L-agar plates containing ampicillin. Several ampicillin resistant colonies were selected, plasmid DNA isolated and examined by restriction analysis. This analysis confirmed the presence of the trp E gene and the loss of the alternator region. One of the plasmids with these characteristics, designated pCT37, was selected for further work involving the human calcitonin gene.

CALCITONIN AND CALCITONIN-GLY FUSIONS WITH TRP E

Figure 11A:
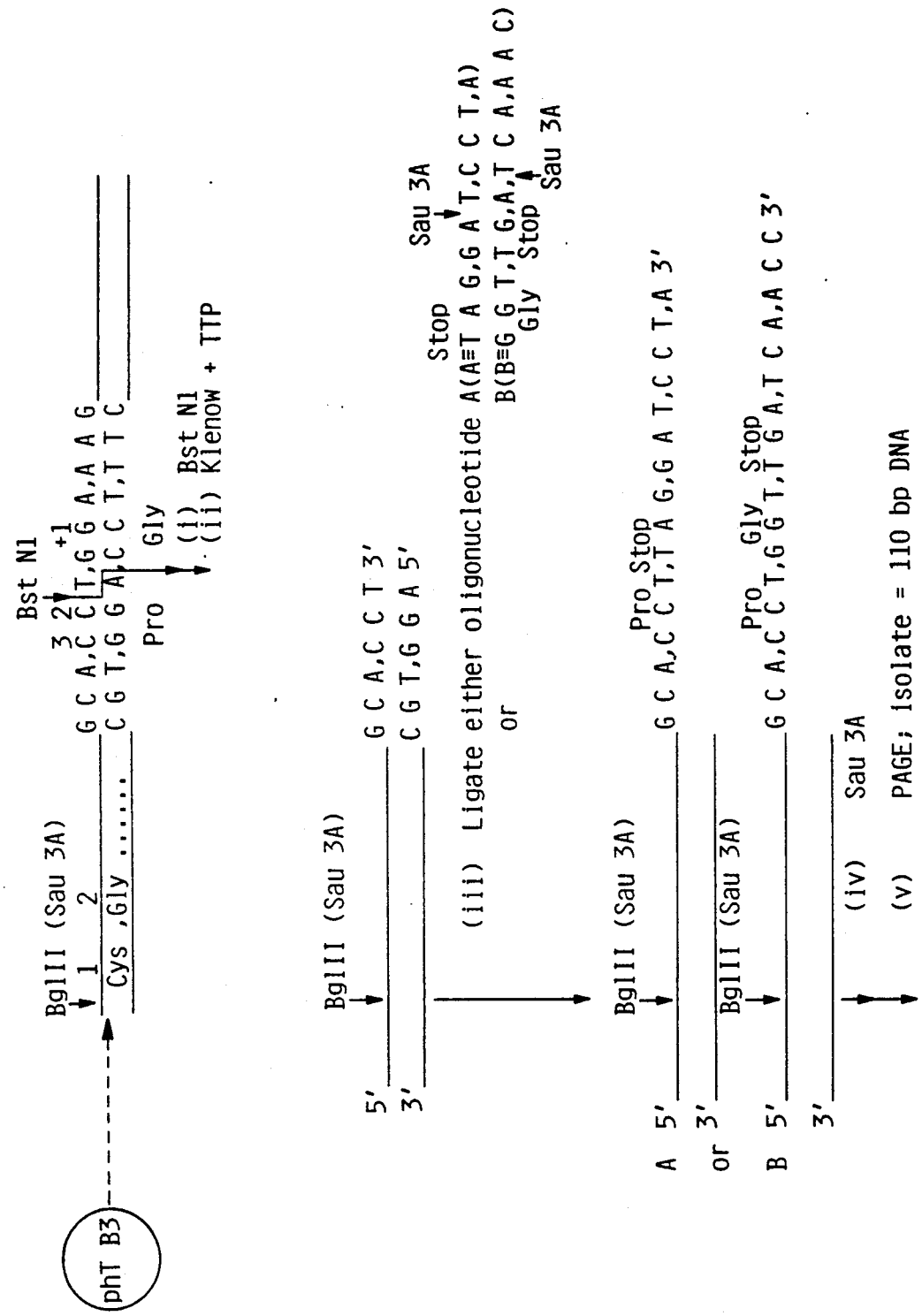
FIGS. 11A and 11B schematically depict the steps carried out to combine the human calcitonin sequence derived from the plasmid phT-B3 with the expression vector pCT37.
Figure 11B:
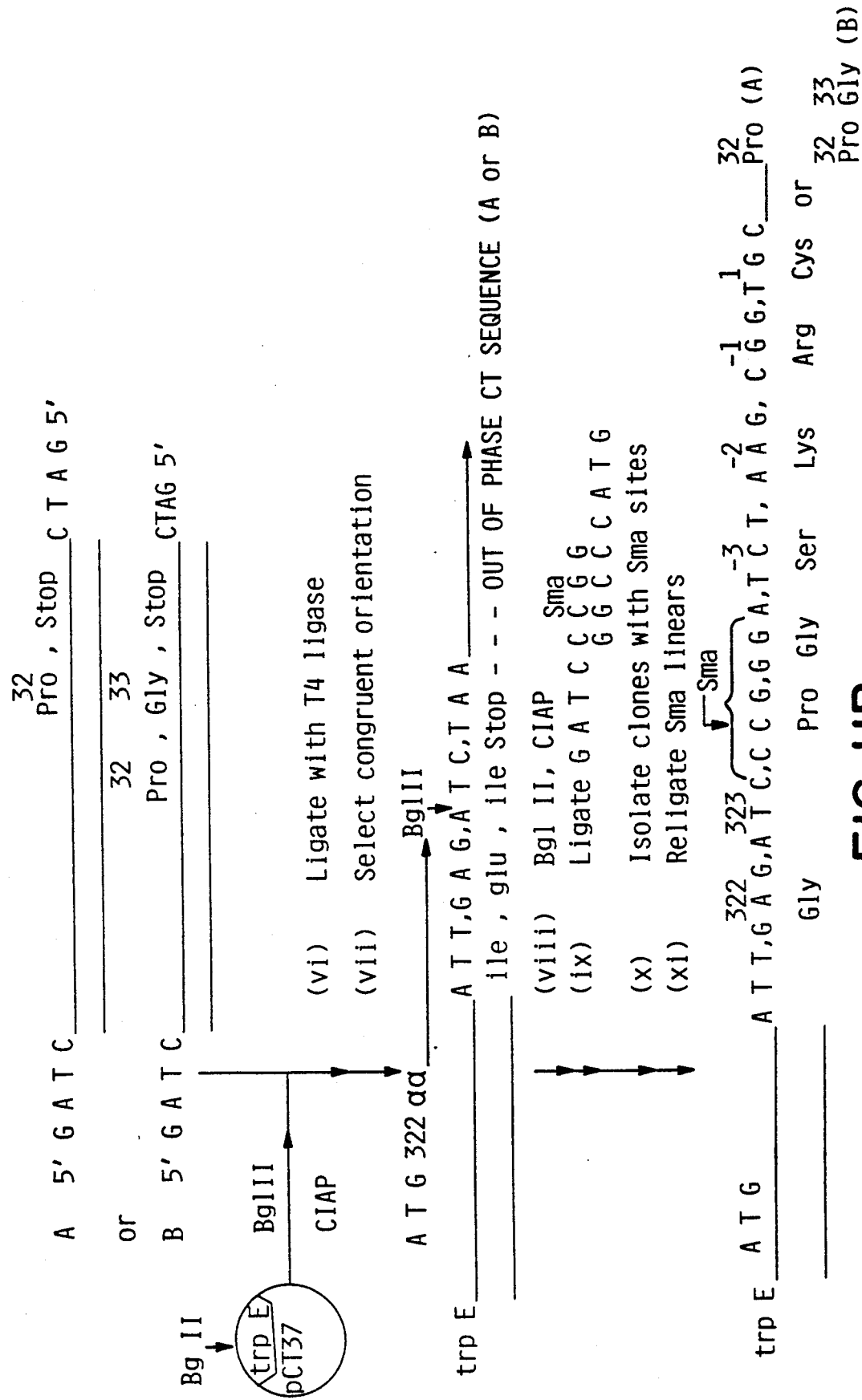

The scheme outlined in FIG. 11 shows the steps carried out to combine the human calcitonin sequence derived from plasmid phT-B3 with the expression vector pCT37 described above to produce fusion proteins. The initial step involves the modification of the calcitonin sequence so that the ultimate amino acid in the fusion protein is either the proline corresponding to the authentic terminal amino acid in calcitonin or so that a further glycine is translated. The purpose of this construction relates to the final processing envisaged in calcitonin production and is described fully below. 20 µg of phT-B3 were incubated in 6 mM Tris-HCl pH 7.5, 6 mM $MgCl_2$, 6 mM $\beta$-mercaptoethanol and 20 mM KCl with 10 units of Bst NI for 60 minutes at 60° C. After incubation the reaction was made 0.3M in NaAcetate pH 6.0, extracted with phenol, then chloroform and concentrated by ethanol precipitation. The precipitated DNA was washed with 70% ethanol, dried under vacuum and redissolved in 20 µl of water (Step i FIG. 11. Bst NI cuts the calcitonin sequence only in the proline at position 32 and in such a way that the T residue in the anti-coding strand is removed. This T residue is added back in the next step (ii). 10 µg of the Bst NI cleaved phT-B3 were incubated in 50 mM Tris-HCl pH 7.6, 10 mM $MgCl_2$, 10 mM $\beta$-mercaptoethanol, 0.2 mM dCTP, 0.2 mM dTTP and 6 units of Klenow enzyme (DNA-polymerase large fragment; supplied by the Boehringer Corporation (London) Ltd). After the incubation the DNA was phenol extracted, chloroform extracted, ethanol precipitated, washed in 70% ethanol and redissolved in 10 µl of water. The resulting DNA is now flush-ended and can be ligated to other flush-ended DNA molecules. The DNA was ligated (covalently joined) with two separate synthetic oligonucleotides designated A or B in FIG. 11.

A = T A G G A T C C T A
      A T C C T A G G A T

B = G G T T G A T C A A C C
      C C A A C T A G T T G G

Thus 2.5 µg of the phT-B3 derived DNA fragments were incubated in separate reactions with 400 ng of oligonucleotides A or B in 60 mM Tris-HCl pH 7.5, 8 mM $MgCl_2$, 10 mM $\beta$-mercaptoethanol, 1 mM ATP and 1.5 µl T4 DNA ligase (New England Biolabs Lot 17) for 24 hours at 16° C. Ligase activity was destroyed by raising the temperature to 70° C. for 5 minutes and the DNA ethanol precipitated, washed in 70% ethanol, dried under vacuum and redissolved in 10 µl of water. 1 µl of both DNA samples (i.e. ligated with oligonucleotide A or B) was analysed for efficient ligation, as evidenced by its increase in size through concatemerisation and visualised by staining an agarose gel with ethidium bromide following an electrophoretic size separation. Note that the two ligation reaction samples represent the start of two separate and parallel construction routes (i.e. A or B) as shown in FIG. 11. The description of the experiments below apply for both series of constructions. The remaining plasmid DNA (9 μl) was separated from unreacted oligonucleotides by Sephadex G-50 chromatography and concentrated by ethanol precipitation. The DNA was redissolved in 50 μl 6 mM Tris-HCl, 50 mM NaCl, 6 mM MgCl$_2$, 6 mM β-mercaptoethanol and excess Sau 3A enzyme added to ensure complete cutting at all Sau 3 sites after 1 hour at 37° C. The linker oligonucleotides contain the Sau 3A recognition sequence 5′ GATC 3′ and the Bgl II site 5′ AGATCT.3′ is also a Sau 3A site so that after the Sau 3A digestion, the calcitonin sequence resides in DNA fragments about 110 base pairs long (the exact length differing by one nucleotide depending on whether oligonucleotide A or B was used). These fragments were isolated following polyacrylamide gel electrophoresis (PAGE) as described above (Step iv FIG. 11) and following ethanol precipitation, were dissolved in water (10 μl). The vector expression plasmid pCT37 (described in detail above) was prepared for their ligation into the Bgl II site as follows. 10 μg of pCT37 was incubated in 6 mM Tris-HCl, 50 mM NaCl, 6 mM MgCl$_2$, 6 mM β-mercaptoethanol and 10 units Bgl II for 60 minutes at 37° C. The linearised DNA was diluted to 0.5 ml and made 0.3M in sodium acetate pH 6.0. 5′ Phosphate groups were removed by the addition of 3 units of calf intestinal alkaline phosphatase (CIAP) and incubation at 60° C. for thirty minutes, after which a further 3 units of CIAP was added and a further 30 minute incubation carried out.

Phosphatase activity was destroyed by one phenol, two phenol-chloroform and three chloroform extractions, after which the DNA was ethanol precipitated and redissolved in water (10 μl). In Step vi the calcitonin containing fragments were ligated into the Bgl II site of pCT37 as follows. 0.1 μg of the Bgl II linearised and CIAP treated pCT37 was incubated with approximately 2 ng of the calcitonin containing fragments in 60 mM Tris-HCl pH 7.5, 8 mM MgCl$_2$, 10 mM β-mercaptoethanol, 1 mM ATP and 0.2 μl T4 DNA ligase (New England Biolabs Lot 17) for 16 hours at 16° C. The DNA was then used to transform frozen competent $E$ $coli$ HB101 using standard methods (cf Methods in Enzymology Vol 68, pp 326–331) and transformants resistant to ampicillin selected on L-ager plates containing 100 μg/ml ampicillin. Clones containing plasmids with the calcitonin sequence in the Bgl II site and in the correct orientation were identified and the constructions confirmed by DNA sequencing using the method of Maxam, A and Gilbert, W Proc Natl Acad Sci 74, 560 (1977). At this stage the calcitonin DNA translation reading frame is out of phase with the trp E gene reading frame and if this reading frame is being used by a ribosome, a stop codon (TAA) will be encountered after amino acid 322 of the trp E gene. Thus in contrast to the parent expression vector pCT37 which directs the overproduction of the trp E gene product, these constructions would be expected to direct the overproduction of a novel truncated protein 323 amino acids long (i.e. about 35K Daltons M Wt).

Figure 12:
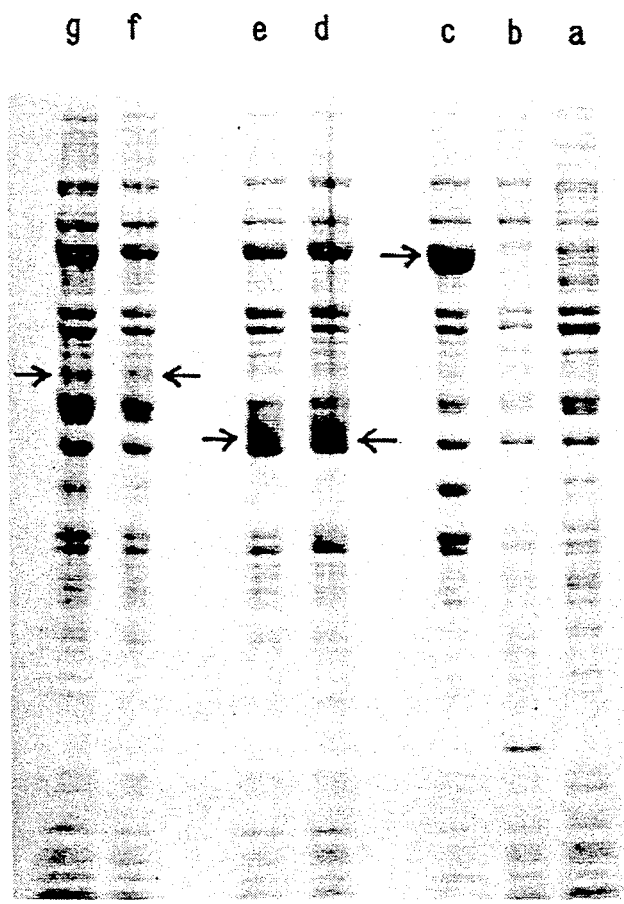
FIG. 12 depicts the novel protein produced by E. coli harboring plasmids of the invention.

That such a novel protein is indeed produced by $E$ $coli$ harbouring these plasmids, and only under appropriate inducing conditions, is illustrated in FIG. 12 (see below). Thus the final steps in the construction of plasmids directing the overproduction of the desired trp E-calcitonin (or calcitonin-gly) fusion proteins requires the calcitonin sequence to be brought into the same translation reading frame as the trp E gene. This can be achieved by adding 3n+2 nucleotides at the fusion junction between the trp E sequence and the calcitonin sequence (i.e. at the recreated unique Bgl II site). The synthetic octomer

```
5′ G A T C C C G G
   G G C C C T A G
```
is suitable since it is of the correct length (8=3×2+2), has an appropriate 5′ overhang for ligation into the Bgl II site and in addition creates a new unique restriction site for the enzyme Sma (5′ CCCGGG 3′) at the fusion junction. Thus the plasmids (10 μg) were incubated in 6 mM Tris-HCl, 50 mM NaCl, 6 mM β-mercaptoethanol, 6 mM MgCl$_2$ with 10 units Bgl II and the phosphate groups removed from the linear molecules using CIAP as described above. Following phenol extraction and ethanol precipitation 0.1 μg of the linear DNA was incubated with a 10-fold molar excess of the synthetic oligonucleotide

```
G A T C C C G G
G G C C T A G    in 60 mμTris-HCl pH 7.5,
```
8 mM MgCl$_2$, 10 mμ β-mercaptoethanol, 1 mM ATP and 0.2 μl T4 DNA ligase, for 16 hours at 16° C. (step ix FIG. 11). The ligation products were used to transform $E. coli$ HB101 cells and ampicillin resistant transformed cloned isolated on L-agar plates containing 100 μg/ml ampicillin.

The majority of plasmids in these clones were found to contain more than one copy of the synthetic oligonucleotide at the fusion junction, 1 μg of plasmids with 2 inserted linkers was linearised by incubation in 6 mM Tris-HCl, 6 mM MgCl$_2$, 6 mM β-mercaptoethanol and 20 mM KCl with 10 units of Sma I (supplied by the Bochringer Corporation (London) Ltd), and following purification of the linear molecules from unlinearised plasmid, the DNA was religated with T4 DNA ligase and following a further round of transformation into HB101 plasmids with the structure shown at the bottom of FIG. 11, were isolated. As illustrated the DNA junction is now such that the calcitonin sequence is in phase with the trp E sequence and such plasmids showed therefore direct the production of a novel fusion protein of the expected size (about 38K Daltons M Wt, see FIG. 12). Verification of these constructions has been demonstrated in the following manner. Thus $E. Coli$ cells harbouring either no plasmids (i.e. HB101 cells described above, FIG. 12 lane a) or harbouring pcT37 (lanes b and c) or harbouring the constructions described above in which a stop codon is found after 323 amino acids (lanes d and e) were grown at 37° C. either in L-broth (lanes a and b) in which the trp promotor is not induced, or in M9-salts in which it is (lanes c,d,e,f,g-see also R. A. Hallewell and J. S. Emtage, Gene 9, 27–47, 1980) and harvested by centrifugation. The cells were dissolved in SDS sample buffer (Laemmli, U.K., Nature 227, 680 (1970). Protein equivalent to 50 μl of original culture was electrophoresed on a 12.5% (w/v) polyacrylamide gel and the separated proteins visualized by staining with coomassie blue. It is clear from FIG. 12 that pcT37 under conditions of Trp promotor induction overproduces the Trp E gene (lane c, indicated by arrow-cf. lane b, where growth is under noninduced conditions). In contrast, in its out of phase calcitonin containing derivatives (lane d has the A type end defined in FIG.

11. while e has the B type end) an appropriate sized novel protein is present as indicated. Where the two constructions contain the calcitonin sequence in phase (lane f in the A-type and lane g the B-type construction) novel proteins of the expected size can be seen.

Figure 13:
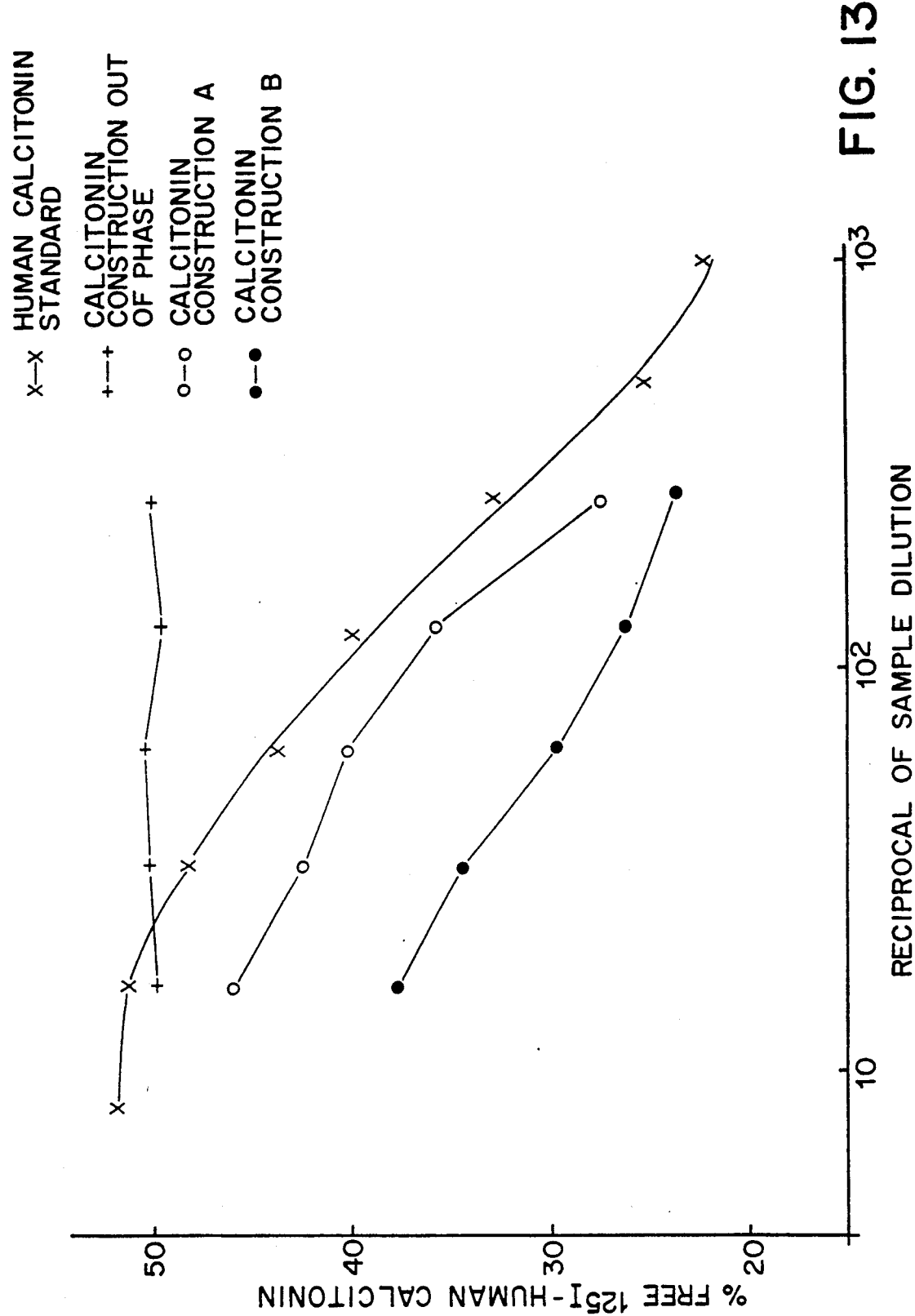
FIG. 13 graphically depicts the presence of the calcitonin peptide in cell lysates from bacterial harboring the plasmids of the invention.

Identification of the presence of the calcitonin peptide with bacterial cell lysates was performed by radio-immunoassay. The assay was carried out essentially as described by SI Girgis et al., (J. Endocrinol 78, 372–382). As can be seen in FIG. 13, dilutions from a lysate of an *E. coli* carrying the calcitonin gene inserted out of phase failed to compete out the $^{125}$I-labelled human calcitonin. In contrast lysates obtained from *E. coli* carrying constructions of the calcitonin gene (both A and B) inserted in phase competed with $^{125}$I-labelled human calcitonin in the expected manner (for comparison compare with calcitonin standard). This confirms that the constructions resulted in the synthesis of a fusion protein containing the expected antigenic determinants of human calcitonin.

CALDITONIN FROM A TRP E-CALCITONIN FUSION PROTEIN

The ultimate aim of introducing the human calcitonin sequence into the trp E gene of *E. coli* in such a way that substantial quantities of a trp E-calcitonin fusion protein are produced is to liberate the calcitonin peptide in a commercially viable way. This may be done by several possible routes. As a first step the calcitonin peptide must be cleaved from the fusion protein. This can be achieved by the use of the enzyme trypsin which will cleave exactly at the fusion junction since the initial cysteine residue is preceded by an arginine. Calcitonin contains no arginines but one lysine residue at position 18 which would also be liable to trypsin cleavage. This lysine can however be protected by citraconic anhydride (Shine S, Fettes I, Nancy C. Y. Lan, Roberts, J. I. and Baxter, J. D. Nature 285, 456–461). The peptide liberated by this procedure differs from authentic calcitonin only in that in authentic calcitonin the C-terminal amino acid is a prolinamide rather than a proline (or proline-glycine) amino acid. Conversion of the liberated peptide into authentic calcitonin is possible through the use of C-terminal modification activity of yeast carboxypeptidase Y (Breddam, K, Widmer, F and Johanson, J. T. Carlsberg Res. Commun. 45, 237–247 and 361–367 1980).

Quite apart from the biological use of calcitonin produced in accordance with the invention, the availability of a cloned human calcitonin cDNA probe, also made possible by the invention, permits comparisons to be drawn between human calcitonin gene structure and expression in normal thyroid tissue, and in familial and sporadic medullary carcinoma of the thyroid. The probes may also be used for definitive studies of the molecular mechanisms involved in the ectopic synthesis of calcitonin, in particular by lung carcinoma, whilst the possibility also arises that cDNA probes may be used to investigate linked DNA polymorphisms, thereby providing a quick and reliable means of distinguishing between familial and sporadic medullary carcinoma of the thyroid, saving patients and their relatives from uncomfortable, extensive and often invasive investigations.

We claim:

1. A process for the production of authentic human calcitonin comprising the steps of:
    i) preparing a polypeptide having the amino acid sequence of human calcitonin-X where —X is an amino acid residue attached by a peptide bond to the proline residue at the C-terminus of the human calcitonin 32 amino acid sequence and is enzymatically processable to —NH$_2$ to produce C-terminal amidated authentic human calcitonin, by culturing a host organism transformed with a vector comprising a structural gene encoding said polypeptide;
    ii) recovering said polypeptide having the amino acid sequence of calcitonin-X; and
    iii) enzymatically processing —X to —NH$_2$ in vitro, to produce authentic human calcitonin.

2. A process for the production of authentic human calcitonin comprising the steps of:
    preparing a fusion polypeptide comprising a host polypeptide and a polypeptide having the amino acid sequence of human calcitonin-X, where —X is an amino acid residue attached by a peptide bond to the proline residue at the C-terminus of the human calcitonin 32 amino acid sequence and is enzymatically processable to —NH$_2$ to produce C-terminal amidated authentic human calcitonin, by culturing a host organism transformed with a vector comprising a structural gene encoding said polypeptide; recovering said fusion polypeptide comprising a host polypeptide and a polypeptide having the amino acid sequence of human calcitonin-X; cleaving the fusion polypeptide; and enzymatically processing —X to —NH$_2$ in vitro, to produce authentic human calcitonin.

3. A process according to claim 2 wherein the said fusion polypeptide is first cleaved and subsequently —X is enzymatically processed to —NH$_2$ in vitro to produce authentic human calcitonin.

4. A process according to claim 2 wherein —X is first enzymatically processed to —NH$_2$ in vitro and the fusion polypeptide is subsequently cleaved to produce authentic human calcitonin.

5. A process according to claim 2 wherein —X is a glycine residue.

6. A process according to claim 3 wherein —X is a glycine residue.

7. A process according to claim 4 wherein —X is a glycine residue.

8. A process for the production of a pharmaceutical composition comprising the steps of:
    i) producing authentic human calcitonin by the process defined in claim 1, and
    ii) admixing said authentic human calcitonin with a pharmaceutically acceptable excipient.

9. A process for the production of a pharmaceutical composition comprising the steps of:
    i) producing authentic human calcitonin by the process defined in claim 2, and
    ii) admixing said authentic human calcitonin with a pharmaceutically acceptable excipient.

10. A process for the production of a pharmaceutical composition comprising the steps of:
    i) producing authentic human calcitonin by the process defined in claim 3, and
    ii) admixing said authentic human calcitonin with a pharmaceutically acceptable excipient.

11. A process for the production of a pharmaceutical composition comprising the steps of:
    i) producing authentic human calcitonin by the process defined in claim 4, and
    ii) admixing said authentic human calcitonin with a pharmaceutically acceptable excipient.

* * * * *